(12) United States Patent
Updyke et al.

(10) Patent No.: US 11,105,769 B2
(45) Date of Patent: Aug. 31, 2021

(54) SYSTEM FOR RAPID HIGH-RESOLUTION GEL ELECTROPHORESIS

(71) Applicant: LIFE TECHNOLOGIES CORPORATION, Carlsbad, CA (US)

(72) Inventors: Timothy Updyke, Temecula, CA (US); Jennifer Miller, Oceanside, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 16/551,364

(22) Filed: Aug. 26, 2019

(65) Prior Publication Data
US 2019/0391113 A1    Dec. 26, 2019

Related U.S. Application Data

(62) Division of application No. 12/862,509, filed on Aug. 24, 2010, now abandoned.

(60) Provisional application No. 61/236,293, filed on Aug. 24, 2009.

(51) Int. Cl.
*G01N 27/447*    (2006.01)
*G01N 33/561*    (2006.01)

(52) U.S. Cl.
CPC ..... *G01N 27/44747* (2013.01); *G01N 33/561* (2013.01)

(58) Field of Classification Search
CPC .......... G01N 27/447; G01N 27/44704; G01N 27/44747; G01N 27/44756–453; G01N 33/561; B01L 2400/0421; B01D 57/00–02

USPC ................. 204/450–465, 600–650; 435/6.11
See application file for complete search history.

(56) References Cited

U.S. PATENT DOCUMENTS

| | | | |
|---|---|---|---|
| 4,948,480 | A | 8/1990 | Christy, Jr. et al. |
| 4,950,708 | A | 8/1990 | Hochstrasser |
| 5,159,049 | A | 10/1992 | Allen |
| 5,275,708 | A | 1/1994 | Akins, Jr. et al. |
| 5,354,442 | A | 10/1994 | Allen et al. |

(Continued)

FOREIGN PATENT DOCUMENTS

| | | |
|---|---|---|
| AU | 698145 B2 | 10/1998 |
| CA | 2186120 A1 | 10/1995 |

(Continued)

OTHER PUBLICATIONS

Sigma-Aldrich, Buffer Reference Center, <http://www.sigmaaldrich.com/life-science/core-bioreagents/biological-buffers/learning-center/buffer-reference-center.html>, last accessed Sep. 4, 2017.*

(Continued)

*Primary Examiner* — Maris R Kessel

(57) ABSTRACT

Electrophoretic systems, formulations and methods are described which allow a user to perform electrophoresis experiments under conditions of high voltage and with reduced run time. An electrophoretic system, formulation or method may be run at 50% higher field strength than comparable systems already in use in the art. The presently described systems and formulations may be run at voltages above 225 V, above 250 V, above 275 V, above 300 V, above 325 V or above 350 V. The time required for performing an electrophoresis experiment may be reduced to less than about 30 minutes, less than about 20 minutes, less than about 15 minutes or less than about 12 minutes.

26 Claims, 15 Drawing Sheets

(56) References Cited

U.S. PATENT DOCUMENTS

| | | | |
|---|---|---|---|
| 5,464,516 | A | 11/1995 | Takeda et al. |
| 5,464,517 | A | 11/1995 | Hjerten et al. |
| 5,543,097 | A | 8/1996 | Fang |
| 5,578,180 | A | 11/1996 | Engelhorn et al. |
| 5,840,877 | A | 11/1998 | Kozulic |
| 5,922,185 | A | 7/1999 | Updyke et al. |
| 6,059,948 | A | 5/2000 | Updyke et al. |
| 6,096,182 | A | 8/2000 | Updyke et al. |
| 6,143,154 | A | 11/2000 | Updyke et al. |
| 6,162,338 | A | 12/2000 | Updyke et al. |
| 6,726,821 | B1 | 4/2004 | Suzuki |
| 6,733,647 | B2 | 5/2004 | Chan et al. |
| 6,783,651 | B1 | 8/2004 | Updyke et al. |
| 7,422,670 | B2 | 9/2008 | Updyke et al. |
| 7,452,453 | B2 | 11/2008 | Updyke et al. |
| 7,892,409 | B2 | 2/2011 | Updyke et al. |
| 7,967,966 | B2 | 6/2011 | Updyke et al. |
| 2002/0134680 | A1 | 9/2002 | Cabilly et al. |
| 2010/0051462 | A1 | 3/2010 | Rowell et al. |
| 2011/0127166 | A1 | 6/2011 | Updyke et al. |

FOREIGN PATENT DOCUMENTS

| | | |
|---|---|---|
| EP | 0566784 A1 | 10/1993 |
| EP | 0753142 A1 | 1/1997 |
| EP | 1911776 B1 | 12/2009 |
| EP | 2183583 B1 | 6/2011 |
| WO | WO-199527197 A1 | 10/1995 |
| WO | WO-2009027983 A1 | 3/2009 |
| WO | WO-2011028535 A2 | 3/2011 |

OTHER PUBLICATIONS

Bellini, "The use of poly(2-acrylamido-2methyl-1 propanesulfonic acid) polymers as spacers for isotachophoresis in sieving gel matrices", Anal Biochem., vol. 1, No. 268, 1999, pp. 21-29.

EP10814248.0, Extended Search Report, dated Jan. 15, 2013, 4 pages.

Fling et al., "Peptide and Protein Molecular Weight Determination by Electrophoresis Using a High-Molarity Tris Buffer System without Urea" Analytical Biochemistry, vol. 155, No. 1, 1986, pp. 83-88.

Garfin, "Gel Electrophoresis of Proteins," 1 DE Web Article, Sep. 2007.

Hjelmeland et al., "The impact of L.G. Longsworth (1905-1981) on the theory of electrophoresis", Electro(2horesis, vol. 3, 1982, pp. 9-17.

Invitrogen, "Overview for Electrophoresis and Western Blotting", Online Informational Material downloaded Mar. 17, 2013; 4 pages.

Mal et al., "SDS disc electrophoresis of proteins in homogeneous, low-concentrated polyacrylamide gels," Electrophoresis vol. 28, 2007; pp. 1508-1513.

Michov, "Electrophoresis in one buffer at two pH values," Electrophoresis, vol. 10, 1989; pp. 686-689.

PCT/US2010/046510, Search Report and Written Opinion, dated Mar. 21, 2011.

Shafer-Nielsen, et al., "A Unifying Model for the Ionic Composition of Steady-State Electrophoresis Systems", Analytical Biochemistry, vol. 114, 1981, pp. 244-262.

Sigma-Aldrich, Biological Buffers,< www.sigmaaldrich.com/life-science/metabolomics/bioultra-reagents/biological-buffers.html>, (last accessed Feb. 22, 2012.

Thermo Scientific, Pierce Protein Biology Products, 1 OX Tris-Glycine-SDS Buffer,< http:www.piercenet.com="" product!trisglycine-sds-buffer-1="" ox="">, last accessed Dec. 8, 2014</http:>.

* cited by examiner

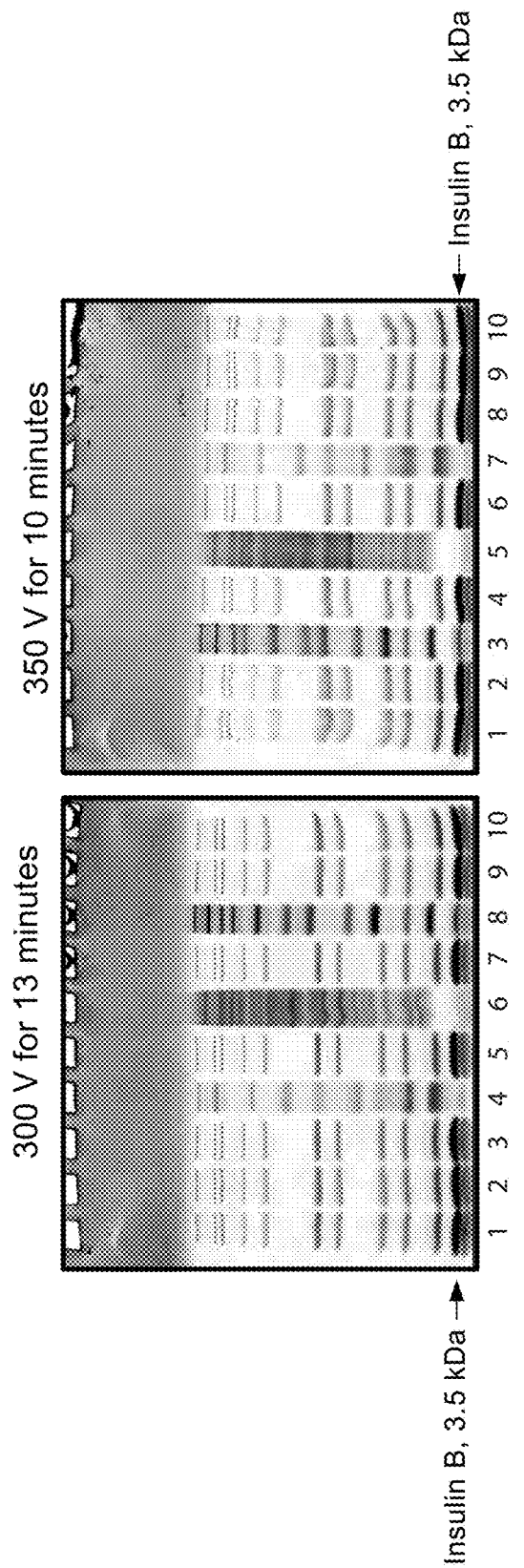
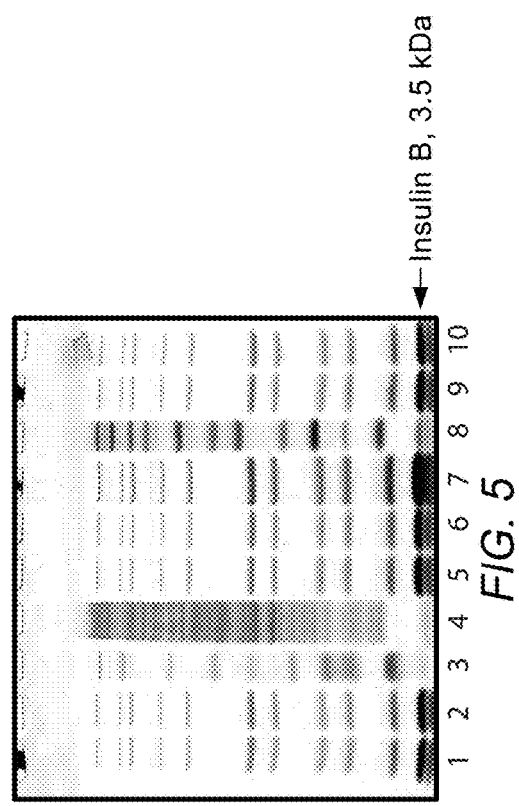

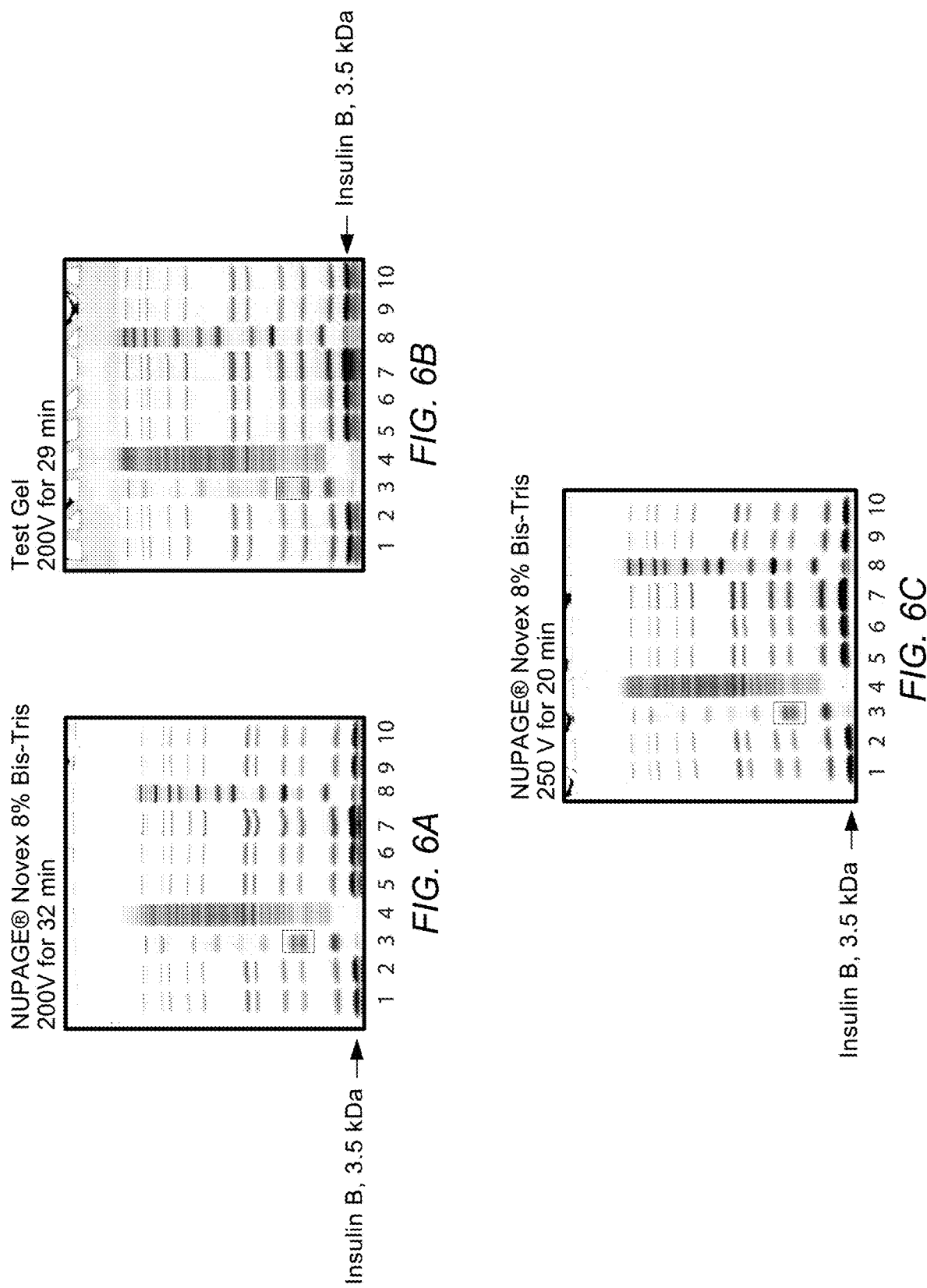

2% Sucrose
12% test gel
15 min, 300V

4% Sucrose
12% test gel
26 min, 300V

SYSTEM FOR RAPID HIGH-RESOLUTION GEL ELECTROPHORESIS

CROSS-REFERENCE TO RELATED APPLICATIONS

This application is a Divisional of U.S. patent application Ser. No. 12/862,509 filed Aug. 24, 2010, which claims the benefit of priority to U.S. Provisional Patent Application No. 61/236,293 filed Aug. 24, 2009, each of which is incorporated by reference herein in its entirety.

BACKGROUND

Field of the Invention

This invention relates to techniques and formulation for use in gel electrophoresis. More particularly, the present invention relates to novel systems and formulations for rapid, high resolution gel electrophoresis at substantially neutral pH.

Description of Related Art

Gel electrophoresis is a common procedure for the separation of biological molecules, such as deoxyribonucleic acid (DNA), ribonucleic acid (RNA), polypeptides and proteins. In gel electrophoresis, the molecules are separated into bands according to the rate at which an imposed electric field causes them to migrate through a filtering gel.

The basic apparatus used in this technique consists of a gel enclosed in a glass tube or sandwiched as a slab between glass or plastic plates. The gel has an open molecular network structure, defining pores which are saturated with an electrically conductive buffered solution of a salt. These pores through the gel are large enough to admit passage of the migrating macromolecules.

The gel is placed in a chamber in contact with buffer solutions which make electrical contact between the gel and the cathode or anode of an electrical power supply. A sample containing the macromolecules and a tracking dye is placed on top of the gel. An electric potential is applied to the gel causing the sample macromolecules and tracking dye to migrate toward the bottom of the gel. The electrophoresis is halted just before the tracking dye reaches the end of the gel. The locations of the bands of separated macromolecules are then determined. By comparing the distance moved by particular bands in comparison to the tracking dye and macromolecules of known size, the size of other macromolecules can be determined.

The rate of migration of macromolecules through the gel depends upon four principle factors: the porosity of the gel; the size and shape of the macromolecule; the charge density of the macromolecule and the applied field strength. Electrophoresis systems generally attempt to control these factors in order to be reproducible from gel to gel and from sample to sample. However, maintaining uniformity between gels is difficult because each of these factors is sensitive to many variables in the chemistry of the gel system.

Polyacrylamide gels are commonly used for electrophoresis. Polyacrylamide gel electrophoresis or PAGE is popular because the gels are optically transparent, electrically neutral and can be made with a range of pore sizes. When used with sodium dodecyl sulfate (SDS), i.e. as SDS-PAGE, the charge density of the macromolecules is controlled by adding sodium dodecyl sulfate (SDS) to the system. SDS molecules associate with the macromolecules and impart a uniform charge density to them, substantially negating the effects of any innate molecular charge.

Historically, SDS-PAGE gels were usually poured and run at basic pH. The most common PAGE buffer system employed for the separation of proteins is that developed by Ornstein and Davis (Ornstein, L. (1964) *Ann. NY Acad. Sci.*, 121: 321 and Davis, B. J. (1964) *Ann. NY Acad. Sci.*: 121: 404), and modified for use with SDS by Laemmli (Laemmli, 1970, *Nature* 227, 680-686). The Laemmli buffer system consists of 0.375 M tris (hydroxymethyl) amino-methane (Tris), titrated to pH 8.8 with HCl, in the separating gel. The stacking gel consists of 0.125 M Tris, titrated to pH 6.8. The anode and cathode running buffers contain 0.024 M Tris, 0.192 M glycine, 0.1% SDS. An alternative buffer system is disclosed by Schaegger and von Jagow (Schaegger, H. and von Jagow, G., *Anal. Biochem.* 1987, 166, 368-379).

U.S. Pat. Nos. 7,422,670; 6,783,651; 6,143,154; 6,059,948; 6,096,182; 6,162,338; 5,922,185; and 5,578,180 by Updyke, et al. describe gel and discontinuous buffer systems where separation occurs at neutral pH and where the proteins remain in a substantially reduced state. The gel systems include a gel amine having a pK in the range of 5.5 to 7.5, and the pH of the gel buffer is in the neutral range (pH 6-8). The gel system exhibits improved stability of the gel matrix and stock solutions. The gels can be stored under refrigeration for over a year without substantial loss of performance. The gel system allows high resolution of proteins that can cover separation range of 2 to 200 kDa. However, the resolution speed of the gel system could be improved and the resolution of these gel formulations deteriorates when field strength is increased by 50%.

There exists a need for electrophoresis gel formulations that can run protein samples on SDS-PAGE gels with significantly reduced run times while maintaining, or increasing, protein resolution with pH neutral discontinuous buffer systems that produce lower conductance while maintaining sufficient buffering capacity to achieve such results using about 50% more field strength than current electrophoresis gel formulations.

SUMMARY

In the presently described embodiments, electrophoretic systems, formulations, kits and methods are described that allow a user to perform electrophoresis experiments under conditions of high voltage and reduced run time. The systems formulations and methods improve upon those already known in the art and allow the user to generate electrophoretically resolved protein samples with a high degree of resolution and a reduced amount of time than currently available systems and formulations. An electrophoretic system, formulation or method practiced in accordance with the presently disclosed embodiments may be run, for example, at 50% higher field strength than comparable systems already in use in the art. In some embodiments, an electrophoresis gel prepared in accordance with the systems, methods and formulations described herein may be run at voltages above 225 V, above 250 V, above 275 V, above 300 V, above 325 V or above 350 V. In some embodiments, an electrophoresis gel prepared in accordance with the systems, methods and formulations described herein may be using a field strength in the range of about 12 v/cm to about 20 v/cm, or at least 12.0-13.0 V/cm, at least 13.5-14 V/cm, at least 15.0-15.5 V/cm, at least 16.0-17.0 V/cm, or at least 17.5-18.5 V/cm.

In some embodiments, the time required for performing an electrophoresis experiment may be reduced to less than about 30 minutes, less than about 20 minutes, less than about 15 minutes or less than about 12 minutes.

In some embodiments, electrophoresis may be performed using the gel formulations that form the basis of the present disclosure using constant current.

In some embodiments, electrophoresis may be performed using the gel formulations that form the basis of the present disclosure using constant power.

An electrophoretic system and method in accordance with the presently described embodiments may be part of a discontinuous buffer system.

An electrophoretic system may include a polyacrylamide electrophoretic separation gel. In some embodiments, a separation gel may include a resolving gel portion and an optional stacking gel portion cast over the resolving portion. In an embodiment, the percentage of polyacrylamide, cross-linker, or both polyacrylamide and cross-linker, present in the stacking portion may be different from the percentage of polyacrylamide and/or cross-linker that is present in the resolving portion.

In an embodiment, the resolving portion may include from about 3% to about 25% polyacrylamide in combination with about 1% to about 6% of a suitable cross-linker such as bis-acrylamide. In an embodiment, the resolving gel portion may be polymerized using from about 2% to about 5% cross-linker. In an embodiment, a resolving gel may include up to about 25% polyacrylamide, up to about 20% polyacrylamide, up to about 15% polyacrylamide, up to about 12% polyacrylamide, up to about 10% polyacrylamide, up to about 8% polyacrylamide, up to about 6% polyacrylamide, or up to about 5% polyacrylamide.

In an embodiment, an electrophoretic separation gel may optionally include, in the stacking portion, the resolving portion, or both the stacking and resolving portions, a density agent such as, e.g., sucrose, glycerol, or a similar non-ionic density agent. The amount of a density agent included in the formulation may be in the range of about 0 to about 10 vol. %, from about 0.5 to about 5 vol. %, from about 1.0 vol. % to about 3.5 vol. %, or about 1.5 vol. % to about 2 vol. %. In an embodiment, the concentration of density present in a gel formulation may be up to about 10 vol. %, up to about 8.5 vol. %, up to about 5 vol. %, up to about 4.5 vol. %, up to about 4 vol. %, up to about 3.5 vol. %, up to about 3 vol. %, up to about 2.5 vol. %, up to about 2 vol. %, up to about 1.5 vol., or up to about 1.0 vol. %.

In an embodiment, at least the resolving gel portion may include a buffer system having a gel amine buffer in combination with a gel ampholyte. In alternate embodiments, both the stacking gel portion and the resolving gel portion may include a gel amine buffer in combination with a gel ampholyte.

A variety of gel amine buffers may be used in the preparation of the gel composition described herein. Gel amine buffers particularly suited for use with the subject electrophoretic separation gels and systems may include primary organic amines or substituted amines. The $pK_a$ range of the gel amine buffer may be near neutrality, typically in the range of about 5 to about 8, in the range of about 5.5 to about 7.5, in the range of about 6 to about 7, in the range of about 6.2 to about 6.8, or about 6.5. Exemplary though non-limiting gel amines buffers suitable for use with the electrophoretic systems and methods described herein may include Bis(2-hydroxyethyl)-imino-tris(hydroxymethyl)-methane (hereinafter "Bis-Tris"), 1,3-bis(tris(hydroxymethyl)methylamino)propane (hereinafter "Bis-Tris propane"), tris(hydroxymethyl)aminomethane (hereinafter "Tris"), triethaniolamine, or any derivatives or salts thereof having a pKa value in the range of about 5.5 to about 7.5.

In some embodiments, the concentration of gel amine buffer present in the gel may be in the range of about 150 mM to about 350 mM, or in the range of about 165 mM to about 325 mM. Typically, the concentration of gel amine buffer present in the gel may be less than about 300 mM. In certain non-limiting embodiments, the concentration of gel amine buffer present in a gel may be in the range of about 175 mM to about 300 mM, or about 190 mM to about 295 mM. In some embodiments, the gel amine buffer selected may be immobilized in the gel matrix after the polymerization of acrylamide components to form the polyacrylamide matrix.

In some embodiments, gel ampholytes particularly suited for use with the subject electrophoretic separation gels and systems may include any biological buffer having an amine group and which is capable of forming zwitterions in aqueous solution. In some embodiments, gel ampholytes that are well-suited for use with the subject gel formulation will have a pK value that is about 1.5 pH units larger than the pKa value of the gel amine. By way of non-limiting example, the following exemplary gel ampholytes are contemplated for use with the presently described embodiments: N-(Tri(hydroxymethyl)methyl)glycine (hereinafter "tricine"), N,N-Bis(2-hydroxyethyl)glycine; Diethylolglycine (hereinafter "bicine"), piperazine-N,N'-bis(2-ethanesulfonic acid) (hereinafter "PIPES"), 3-(N-Morpholino)-2-hydroxypropanesulfonic Acid (hereinafter "MOPSO"), N-(2-Acetamido)-2-aminoethanesulfonic acid (hereinafter "ACES"), N,N-Bis(2-hydroxyethyl)-2-aminoethanesulfonic acid (hereinafter "BES"), N-Tris(hydroxymethyl)methyl-2-aminoethanesulfonic acid (hereinafter "TES"), -(2-hydroxyethyl)-1-piperazineethanesulfonic acid (hereinafter "HEPES"), 2-amino-methyl-1,3-propanediol 3-[4-(2-Hydroxyethyl)-1-piperazinyl]propanesulfonic acid (hereinafter "HEPPS"), and N-Tris(hydroxymethyl)methyl-3-aminopropanesulfonic acid (hereinafter "TAPS"). Of course, it will be readily apparent to those skilled in the art that any gel ampholyte having at least one amine or substituted amine and further having a pKa that is about 1.5 pH units greater than the gel amine chosen for use in the gel may be used in the practice of the presently described embodiments, without departing from the spirit and scope thereof. An ampholyte may be present in a gel formulation at a concentration in the range of about 25 mM to about 175 mM, about 45 mM to about 100 mM, about 50 mM to about 75 mM or about 50 mM to about 60 mM.

In some embodiments, the subject electrophoretic separation gels and systems may be titrated with an appropriate acid such that the desired pH of the electrophoresis gel is achieved. In an embodiment, a sufficient amount of acid may be used such that the pH of the electrophoresis gel is substantially neutral (i.e., in the range of about pH 5.5 to about pH 7.5). In an embodiment, a sufficient amount of acid may be used such that the pH of the electrophoresis gel is in the range of about pH 5.5 to about pH 7.5, in the range of about pH 6 to about pH 7, or in the range of about pH 6.2 to about pH 6.8. In an embodiment, a sufficient amount of acid may be used to adjust the pH of the electrophoresis get to substantially neutral, e.g., pH of about 6.2, about 6.3, about 6.4, about 6.5, about 6.6, about 6.7, about 6.8, about 6.9, about 7.0, about 7.1, or about 7.2. Typically, though not exclusively, the acid chosen may include a source of anions, such as chloride ions, phosphate ions, sulfate ions or acetate ions. The anions present in the gel formulation may act, in part, as a source of leading ions for a discontinuous gel system. An exemplary though non-limiting acid suitable for use in titrating the gel buffer system of the present embodiments is hydrochloric acid (HCl). In an embodiment, an electrophoresis gel may be titrated with approximately half as much HCl (on a molar basis) as the primary amine and/or the ampholyte, so that the pH of the buffer is approximately neutral. In some embodiments, the final concentration of chloride ions used to titrate an electrophoresis gel may be in the range of about 95 mM to about 175 mM, from about 120 mM to about 160 mM, from about 135 mM to about 145 mM, or about 140 mM.

In an embodiment, an electrophoretic system may additionally include an aqueous running buffer. The aqueous running buffer may include a running buffer ampholyte. In an embodiment, the running buffer may include an ampholyte that is different from the gel ampholyte. In an embodiment, a running buffer ampholyte may include at least one organic buffer ampholyte having at least one amine group. In an embodiment, the pKa of a running buffer ampholyte that is particularly suited for use with the presently described systems and methods will be lower than the pKa of the gel buffer ampholyte.

In some embodiments, an aqueous running buffer ampholyte that is chosen for use with the subject electrophoresis systems may form the basis of a discontinuous buffer system. In such a system, the buffer ampholyte may function, in part, as a source of trailing ions for a discontinuous buffer system.

Non-limiting examples of aqueous running buffer ampholytes that are suitable for use with the presently described systems and methods include 3-(N-morpholino) propanesulfonic acid ("MOPS"), 2-(N-morpholino) ethanesulfonic acid (MES), 3-[N,N-bis(2-Hydroxyethyl)amino]-2-hydroxypropanesulfonic Acid (hereinafter "DIPSO"), N'-bis (2-hydroxypropanesulfonic acid) ("POPSO"), HEPPS, N-(2-Hydroxyethyl)piperazine-N'-2-hydroxypropanesulfonic Acid ("HEPPSO"), or 3-[N-Tris(hydroxymethyl)methylamino]-2-hydroxypropanesulfonic Acid ("TAPSO"), or any suitable salts thereof. Typically, the amount of ampholyte present in an aqueous running buffer will be in the range of about 10 mM to about 100 mM, about 15 mM to about 75 mM, about 25 mM to about 50 mM or about 40 mM to about 45 mM. The running buffer may optionally include an additional buffering agent such as Tris, in addition to SDS and/or EDTA. An exemplary though non-limiting example of a running buffer well suited for use with the presently disclosed embodiments may include 25-100 mM MES, 25-100 mM Tris, about 0.05 to about 0.5 SDS and about 0.5 mM to about 2 mM EDTA.

In some embodiments, discontinuous buffer electrophoretic systems prepared in accordance with the presently described systems and methods may be run at voltages exceeding 250 V and achieve full resolution of the sample in less than 30 minutes. In some embodiments, an electrophoresis gel prepared in accordance with the presently described systems and formulations may be run at voltages above 225 V, above 250 V, above 275 V, above 300 V, above 325 V or above 350 V. In some embodiments, the time required for performing an electrophoresis experiment using the systems and methods and gels described may be reduced to less than about 30 minutes, less than about 20 minutes, less than about 15 minutes or less than about 12 minutes.

In some embodiments, electrophoresis may be performed using the gel formulations that form the basis of the present disclosure using constant current. For example, in some embodiments, the subject gel formulations may be subjected to electrophoresis using a constant current up to about 200 mA, up to about 175 mA, up to about 150 mA, up to about 125 mA, or up to about 115 mA.

Samples subjected to electrophoresis using the subject electrophoretic separation systems and formulation under such conditions may achieve substantially comparable resolution as gel formulations currently in use.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 4A shows a representative test gel according to one embodiment, in which a 4% stacking gel having 178 mM Bis-Tris, 105 mM Cl⁻, pH 6.5 is cast over an 8% resolving gel (S:R=1:3) having 178 mM Bis-Tris, 105 mM Cl⁻, no Tricine, and 4 wt. % sucrose. 5 µl Mark12™ protein marker was loaded in lanes 1-3, 5, 7, 9 and 10, 5 µl SeeBlue Plus2® Pre-Stained Protein Standard was loaded in lane 4, 10 µg *E. coli* lysate was loaded in lane 6, and 5 µl Novex® Sharp Pre-Stained Protein Standard was loaded in lane 8 and the gel was run in MES SDS Running Buffer at 300 V for 13 minutes and stained with SimplyBlue™ SafeStain;

FIG. 4B shows a representative test gel according to one embodiment, in which a 4% stacking gel having 178 mM Bis-Tris, 105 mM Cl⁻, pH 6.5 is cast over an 8% resolving gel (S:R=1:3) having 178 mM Bis-Tris, 105 mM Cl⁻, no Tricine, and 4 wt. % sucrose. 5 µl Mark12™ protein marker was loaded in lanes 1-3, 5, 7, 9 and 10, 5 µl SeeBlue Plus2® Pre-Stained Protein Standard was loaded in lane 4, 10 µg *E. coli* lysate was loaded in lane 6, and 5 µl Novex® Sharp Pre-Stained Protein Standard was loaded in lane 8 and the gel was run in MES SDS Running Buffer at 350 V for 10 minutes and stained with SimplyBlue™ SafeStain;

FIG. 5 shows a representative test gel according to one embodiment, in which a 4% stacking gel having 228 mM Bis-Tris, 210 mM Cl⁻, 50 mM Tricine, 0% sucrose, pH 6.5 was cast over an 8% resolving gel (S:R=1:4) having 228 mM Bis-Tris, 140 mM C⁻, 50 mM Tricine, and 4 wt. % sucrose and no BES. 5 µl Mark12™ protein marker was loaded in lanes 1, 2, 5-7, 9 and 10, 5 μl SeeBlue Plus2® Pre-Stained Protein Standard was loaded in lane 3, 10 μg *E. coli* lysate was loaded in lane 4, and 5 μl Novex® Sharp Pre-Stained Protein Standard was loaded in lane 8, the gel was run in MES SDS Running Buffer at 300 V for 13 minutes and stained with SimplyBlue™ SafeStain;

FIG. 6A shows a representative NuPAGE® Novex 8% Bis-Tris gel with 5 μl Mark12™ protein marker loaded in lanes 1, 2, 5-6, 9 and 10, 5 μl SeeBlue Plus2® Pre-Stained Protein Standard loaded in lane 3, 10 μg *E. coli* lysate loaded in lane 4, 10 μl Mark12™ protein marker loaded in lane 7, and 5 μl NOVEX® Sharp Pre-Stained Protein Standard loaded in lane 8, run in MES SDS Running Buffer at 200 V for 32 minutes and stained with SimplyBlue™ SafeStain;

FIG. 6B shows a representative test gel according to one embodiment, in which a 4% stacking gel having 228 mM Bis-Tris, 140 mM Cl⁻, 50 mM Tricine, 0% sucrose, pH 6.5 is cast over an 8% resolving gel (S:R=1:4) having 228 mM Bis-Tris, 140 mM Cl⁻, 50 mM Tricine, 4% sucrose, and no BES, where 5 μl Mark12™ protein marker is loaded in lanes 1, 2, 5-6, 9 and 10, 5 μl SeeBlue Plus2® Pre-Stained Protein Standard is loaded in lane 3, 10 μg *E. coli* lysate is loaded in lane 4, 10 μl Mark12™ protein marker loaded in lane 7, and 5 μl Novex® Sharp Pre-Stained Protein Standard is loaded in lane 8, and the gel is run in MES SDS Running Buffer at 200 V for 29 minutes and stained with SimplyBlue™ SafeStain;

FIG. 6C shows a representative NuPAGE® Novex 8% Bis-Tris gel with 5 μl Mark12™ protein marker loaded in lanes 1, 2, 5-6, 9 and 10, 5 μl SeeBlue Plus2® Pre-Stained Protein Standard loaded in lane 3, 10 μg *E. coli* lysate loaded in lane 4, 10 μl Mark12™ protein marker loaded in lane 7, and 5 μl Novex® Sharp Pre-Stained Protein Standard loaded in lane 8, run in MES SDS Running Buffer at 250 V for 20 minutes and stained with SimplyBlue™ SafeStain;

Figure 1:
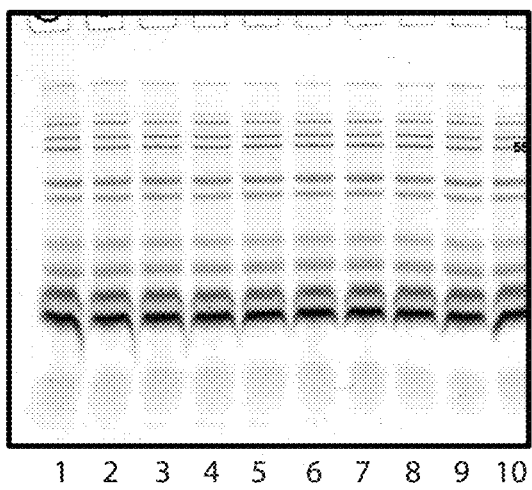
FIG. 1 shows a representative test gel according to one embodiment, in which a 4% stacking gel having 357 mM Bis-Tris, 210 mM Cl⁻, pH 6.5 is cast over an 8% resolving gel (S:R=1:4) having 100 mM Bis-Tris, 75 mM Tricine, 4 wt. % sucrose and 20 mM BES. 5 µl of Mark12™ protein marker was resolved at 300 V for 15 min in MES SDS running buffer, and the gel was stained with SimplyBlue™ SafeStain.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

Definitions

The terms used throughout this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not preclude the use of other synonyms. The use of examples anywhere in this specification, including examples of any terms discussed herein, is illustrative only, and in no way limits the scope and meaning of any of the embodiments set forth herein or of any exemplified term.

As used herein, the term "discontinuous buffer", "discontinuous system" and "discontinuous buffer system" generally refer to one of two aqueous buffering systems used in polyacrylamide gel electrophoresis systems. A discontinuous buffer system is functionally and chemically distinguished from a continuous buffer system. Typically, a continuous system has only a single separating gel and uses the same buffer in the tanks and the gel. In a discontinuous system, a non-restrictive large pore gel, called a stacking gel, is layered on top of a separating gel (sometimes referred to as a "resolving gel"). Each gel may be made with the same, or different, buffer, and the tank buffers are different from the gel buffers. The discontinuity is created by the difference in ion mobility of the faster moving leading ion (for example, chloride) and the slower moving trailing ion (MES, MOPS, glycine or tricine). The resolution obtained in a discontinuous system is much greater than that obtained with a continuous system for samples that contain dilute solutions of analytes due to the concentrating effect of discontinuous systems to create sharp starting zones of analyte molecules. The difference between a continuous buffer system and a discontinuous buffer system is well known to those skilled in the art to which the present invention pertains.

The term "band sharpness" is a relative term that is used to compare the sharpness of migrated bands as they appear on various gel formulations. The term is used particularly when comparing relative band sharpness between two or more of various gel formulations. A variety of methods may be used to determine band sharpness. For example, depending on the degree of resolution that is obtained, band sharpness, or the degree to which band sharpness is improved, may be determined by visual inspection. To obtain a more quantitative estimation of band sharpness, a user may employ gel imaging software. An exemplary though non-limiting gel analysis software typically used in the art is, e.g., TOTALLAB™ software (Nonlinear Dynamics Ltd, Durham, N.C.), GEL-PRO™ Analyzer (Media Cybernetics, Bethesda, Md.) or LABIMAGE® 1D L300 Gel Analysis software (LabImage, Leipzig, Germany). Band sharpness may be determined by measuring the area of each resolved band in a gel, and dividing the area by the width of each well (which is generally constant). Another method of determining band sharpness may be to directly measure the width of individual peaks detected by the gel analysis algorithm.

Electrophoretic systems, formulations and methods are described herein that allow a user to perform electrophoresis experiments under conditions of high voltage and reduced run time. The systems formulations and methods improve upon those already known in the art and allow the user to generate electrophoretically resolved proteins with a high degree of resolution and a reduced amount of run time than currently available systems and formulations. An electrophoretic system, formulation or method practiced in accordance with the presently disclosed embodiments may be run at 50% higher field strength than comparable systems already in use in the art. By way of example, an electrophoresis gel prepared in accordance with the presently described systems and formulations may be run at voltages above 225 V, above 250 V, above 275 V, above 300 V, above 325 V or above 350 V. The time required for performing the electrophoresis may be reduced to less than about 30 minutes, less than about 20 minutes, less than about 15 minutes or less than about 12 minutes. In some embodiments, electrophoresis may be performed using the gel formulation that forms the basis of the present disclosure using constant current. For example, in some embodiments, the subject gel formulations may be subjected to electrophoresis using a constant current of up to about 200 mA, up to about 175 mM, up to about 150 mM, up to about 125 mM, or up to about 115 mM.

In an embodiment, an electrophoretic system may include a gel and buffer system wherein separation occurs at substantially neutral pH. Without being bound by any particular theory or mechanism, it is believe that the use of a neutral pH electrophoretic system ensures that biological molecules within a sample being subjected to electrophoresis (e.g., proteins, nucleic acids, carbohydrates and the like) remain completely or substantially reduced and unhydrolyzed. Advantageously, at neutral pH, primary amino groups of proteins are less reactive with unpolymerized acrylamide, thereby allowing greater resolution and improved band sharpness. Additionally, at neutral pH, thiol groups are less susceptible to oxidation than under the more alkaline conditions under which SDS-PAGE is traditionally performed. The gel formulations that form the basis of the present disclosure may, in some embodiments, function optimally when used as part of a discontinuous buffer system. A discontinuous buffer system is one using a different aqueous buffer in the anode chamber, the cathode chamber, or both the anode and the cathode chambers from the buffer present in the gel. The concentration of the aqueous running buffer may be different from the buffer concentration of the electrophoresis gel. In some embodiments, a gel formulation in accordance with the present disclosure may include a stacking gel and a resolving gel.

The resulting gel electrophoresis systems display improved stability of the gel matrix and buffer solutions at high voltages, and thereby allow gel electrophoresis to be performed at higher voltage than traditional electrophoretic systems, without compromising band resolution. Gels prepared in accordance with the presently described formulations and methods can be stored under refrigeration for at least up to about sixteen months without loss of performance. Additionally, stock buffers and stock gel solutions without polymerization initiator can be stored for several weeks or more at room temperature, with no loss of performance. Using the systems and methods described herein, an 8% polyacrylamide gel, for example, can resolve a protein sample in a separation range of about 2 to 250 kDa in less than 15 minutes.

In some embodiments, a gel formulation may include a stacking gel and a resolving gel. The ratio of stacking gel to resolving gel (also denoted as S:R) may be about 0.5:9.5, about 1:9, about 1.5:8.5, about 2:8, about 2.5:7.5, about 3:7, about 3.5:6.5, about 4:6, about 4.5:5.5, or about 1:1. The meaning of the term stacking and resolving gel, when used in the context of a discontinuous gel electrophoresis system, is well known to a practitioner having ordinary skill in the art. Typically, the percentage of polyacrylamide and/or cross linker (for example, bis-acrylamide) that is present in a stacking gel may be less than the percentage of polyacrylamide and/or cross linker that is present in a resolving gel. In some embodiments, the percentage of polyacrylamide that is present in a stacking gel will be less than about 6%, less than about 5%, less than about 4%, less than about 3%.

In one embodiment of an electrophoretic system and formulation, a resolving polyacrylamide gel of between about 3% and about 25% (% T) acrylamide is polymerized using about 1% to about 6% of a suitable crosslinker (% C) such as bisacrylamide. In an embodiment, the gel is polymerized using from about 2% to about 5% crosslinker (% C) in the presence of a gel buffer. In an embodiment, a polyacrylamide gel may include 25% acrylamide, 24% acrylamide, 23% acrylamide, 22% acrylamide, 21% acrylamide, 20% acrylamide, 19% acrylamide, 18% acrylamide, 17% acrylamide, 16% acrylamide, 15% acrylamide, 14% acrylamide, 13% acrylamide, 12% acrylamide, 11% acrylamide, 10% acrylamide, 9% acrylamide, 8% acrylamide, 7% acrylamide, 6% acrylamide, or 5% acrylamide.

In an embodiment of an electrophoretic system and formulation, a reducing agent may optionally be included in one or more of the gel, the buffer or the loading buffer, so as to maintain a chemically reducing environment. A variety of suitable reducing agents are known in the art, any of which are suitable for use with the embodiments disclosed herein. By way of non-limiting example, a reducing agent such as thioglycolic acid (TGA) or sodium bisulfate may be added to the formulation. Suitable concentration ranges for such reducing agents may be from about 0.5 mM to about 20 mM, from about 1 mM to about 15 mM, from about 2 mM to about 10 mM or from about 5 mM to about 7.5 mM. In some embodiments that include an optional reducing agent, the reducing agent may be added to the gel running buffer.

In certain non-limiting though preferred embodiments, the SDS may be substantially absent from the electrophoresis gel and may instead by provided in the running buffer and/or the loading buffer. A variety of suitable running buffers are described in detail below.

In some embodiments, a polyacrylamide gel in accordance with the presently described embodiments may include primary organic amine or mono- or di-substituted amine buffers. The $pK_a$ range of the gel amine buffer can be near neutrality, typically in the range of about 5 to about 8, in the range of about 5.5 to about 7.5, in the range of about 6 to about 7, in the range of about 6.2 to about 6.8, or about 6.5. The $pK_a$ range of the gel amine buffer may be near neutrality, typically in the range of about 5 to about 8, in the range of about 5.5 to about 7.5, in the range of about 6 to about 7, in the range of about 6.2 to about 6.8, or about 6.5. Exemplary though non-limiting gel amines buffers suitable for use with the electrophoretic systems and methods described herein may include Bis(2-hydroxyethyl)-imino-tris(hydroxymethyl)-methane (hereinafter "Bis-Tris"), 1,3-bis(tris(hydroxymethyl)methylamino)propane (hereinafter "Bis-Tris propane"), tris(hydroxymethyl)aminomethane (hereinafter "Tris"), triethaniolamine, or any derivatives or salts thereof having a pKa value in the range of about 5.5 to about 7.5. Of course, it will be readily apparent to those skilled in the art that any gel amine buffer having at least one primary amine or substituted amine and further having a pKa in the range of 5.5 to 7.5 may be used during the practice of the presently described embodiments, without departing from the spirit and scope thereof.

In some embodiments, the concentration of gel amine buffer present in the gel may be in the range of about 150 mM to about 350 mM, or in the range of about 165 mM to about 325 mM. Typically, the concentration of gel amine buffer present in the gel may be less than about 300 mM. In certain non-limiting embodiments, the concentration of gel amine buffer present in a gel may be in the range of about 175 mM to about 300 mM, or about 190 mM to about 295 mM.

In some embodiments, the gel amine buffer may be added directly to the resolving gel, to the stacking gel, or to both the resolving gel and the stacking gel as an aqueous solution, at the time the other aqueous components thereof are combined and prior to the initiation of the polymerization reaction. Alternatively, the gel amine buffer may be incorporated into the gel matrix by soaking the polymerized gel in an aqueous solution containing the desired concentration of gel amine buffer and allowing the gel amine buffer to permeate the polymerized gel matrix.

In some embodiments, a polyacrylamide gel that forms the basis of an electrophoretic system may include a gel ampholyte in combination with the gel amine described above. A gel ampholyte suitable for use with the subject gel formulations may include, without limitation, any biological buffer having an amine group and which is capable of forming zwitterions in aqueous solution. In some embodiments, gel ampholytes that are well-suited for use with the subject gel formulation will have a pK value that is about 1.5 pH units larger than the pKa value of the gel amine. By way of non-limiting example, the following exemplary gel ampholytes are contemplated for use with the presently described embodiments: N-(Tri(hydroxymethyl)methyl)glycine (hereinafter "tricine"), N,N-Bis(2-hydroxyethyl)glycine; Diethylolglycine (hereinafter "bicine"), piperazine-N,N'-bis(2-ethanesulfonic acid) (hereinafter "PIPES"), 3-(N-Morpholino)-2-hydroxypropanesulfonic Acid (hereinafter "MOPSO"), N-(2-Acetamido)-2-aminoethanesulfonic acid (hereinafter "ACES"), N,N-Bis(2-hydroxyethyl)-2-aminoethanesulfonic acid (hereinafter "BES"), N-Tris(hydroxymethyl)methyl-2-aminoethanesulfonic acid (hereinafter "TES"), -(2-hydroxyethyl)-1-piperazineethanesulfonic acid (hereinafter "HEPES"), 2-amino-methyl-1,3-propanediol 3-[4-(2-Hydroxyethyl)-1-piperazinyl]propanesulfonic acid (hereinafter "HEPPS"), and N-Tris(hydroxymethyl)methyl-3-aminopropanesulfonic acid (hereinafter "TAPS"). Of course, it will be readily apparent to those skilled in the art that any gel ampholyte having at least one amine or substituted amine and further having a pKa that is about 1.5 pH units greater than the gel amine chosen for use in the gel may be used in the practice of the presently described embodiments, without departing from the spirit and scope thereof. An ampholyte may be present in a gel formulation at a concentration in the range of about 25 mM to about 175 mM, about 45 mM to about 100 mM, about 50 mM to about 75 mM or about 50 mM to about 60 mM.

In some embodiments, the gel ampholyte may be added directly to the resolving gel, to the stacking gel, or to both the resolving gel and the stacking gel as an aqueous solution, at the time the other aqueous components thereof are combined and prior to the initiation of the polymerization reaction. Alternatively, the gel ampholyte may be incorporated into the gel matrix by soaking the polymerized gel in an aqueous solution containing the desired concentration of gel ampholyte and allowing the gel ampholyte to permeate the polymerized gel matrix.

In some embodiments, the subject buffered gel systems and formulations may be titrated with an appropriate acid such that the desired pH of the electrophoresis gel is achieved. In an embodiment, a sufficient amount of acid may be used such that the pH of the electrophoresis gel is substantially neutral (i.e., in the range of about pH 5.5 to about pH 7.5). In an embodiment, a sufficient amount of acid may be used such that the pH of the electrophoresis gel is in the range of about pH 5.5 to about pH 7.5, in the range of about pH 6 to about pH 7, or in the range of about pH 6.2 to about pH 6.8. In an embodiment, a sufficient amount of acid may be used to adjust the pH of the electrophoresis get to substantially neutral, e.g., pH of about 6.2, about 6.3, about 6.4, about 6.5, about 6.6, about 6.7, about 6.8, about 6.9, about 7.0, about 7.1, or about 7.2. Typically, though not exclusively, the acid chosen may include a source of anions, such as chloride ions, phosphate ions, sulfate ions or acetate ions. The anions present in the gel formulation may act, in part, as a source of leading ions for a discontinuous gel system. An exemplary though non-limiting acid suitable for use in titrating the gel buffer system of the present embodiments is hydrochloric acid (HCl). In an embodiment, an electrophoresis gel may be titrated with approximately half as much HCl (on a molar basis) as the primary amine and/or the ampholyte, so that the pH of the buffer is approximately neutral. In some embodiments, the final concentration of chloride ions used to titrate an electrophoresis gel may be in the range of about 95 mM to about 175 mM, from about 120 mM to about 160 mM, from about 135 mM to about 145 mM, or about 140 mM.

In some embodiments, anions that function as a leading ion in a discontinuous buffer system may be present in the stacking gel, in the resolving gel, or in both the stacking gel and the resolving. Exemplary though non-limiting leading ions suitable for use in the presently described gel formulation may include anions, such as chloride, phosphate ions, sulfate ions or acetate ions. Sources for such anions may include HCl or any acid halide, phosphoric acid, sulfuric acid, or acetic acid.

In an embodiment, the concentration of leading ion may be higher in the stacking gel than in the resolving gel. In another embodiment, the concentration of leading ion may be substantially the same in the stacking gel as in the resolving gel. In some embodiments, the concentration of leading ion in the stacking gel may be up to about 350 mM, up to about 300 mM, up to about 250 mM, up to about 200 mM, up to about 150 mM, up to about 125 mM, up to about 110 mM, up to about 100 mM or up to about 75 mM.

In some embodiments, an electrophoresis gel in accordance with the presently described embodiments may optionally include a density agent such as, e.g., sucrose, glycerol, or a similar agent. The amount of a density agent included in the formulation may be in the range of about 0 to about 8 wt. %, form about 0.5 to about 5 wt. %, from about 1.0 wt. % to about 3.5 wt. %, or about 1.5 wt. % to about 2 wt. %. In an embodiment, the concentration of sucrose present in a gel formulation may be up to about 10%, up to about 8.5%, up to about 5%, up to about 4.5%, up to about 4%, up to about 3.5%, up to about 3%, up to about 2.5%, up to about 2%, up to about 1.5%, up to about 1% or up to about 0.5%. In some embodiments, the amount of density agent present in an electrophoresis gel may vary. Such embodiments may advantageously be used during the preparation of a gradient gel, such as the methods described in, for example, U.S. Pat. Nos. 6,472,503 and 6,197,173.

The gels prepared in accordance with the formulations disclosed above may be subjected to electrophoresis using an aqueous running buffer system. Typically, the aqueous running buffer system may include at least one buffer ampholyte having at least one amine group. In an embodiment, the running buffer ampholyte that is selected for use with the subject discontinuous electrophoresis system will be different from the gel buffer ampholyte that is present in the electrophoresis gel being used with the aqueous running buffer. In an embodiment, the $pK_a$ of the selected running buffer ampholyte may be less than the $pK_a$ of the gel buffer ampholyte being used.

In certain particularly preferred embodiments, the aqueous running buffer ampholyte that is chosen will preferably form the basis of a discontinuous buffer system. In such a system, the running buffer ampholyte may function, in part, as a source of trailing ions for a discontinuous buffer system. In an embodiment, the pKa of a running buffer ampholyte that is particularly suited for use with the presently described systems and methods will be lower than the pKa of the gel buffer ampholyte.

Non-limiting examples of aqueous running buffer ampholytes that are suitable for use with the presently described systems and methods include 3-(N-morpholino) propanesulfonic acid ("MOPS"), 2-(N-morpholino) ethanesulfonic acid (MES), 3-[N,N-bis(2-Hydroxyethyl)amino]-2-hydroxypropanesulfonic Acid (hereinafter "DIPSO"), N'-bis (2-hydroxypropanesulfonic acid) ("POPSO"), HEPPS, N-(2-Hydroxyethyl)piperazine-N'-2-hydroxypropanesulfonic Acid ("HEPPSO"), or 3-[N-Tris(hydroxymethyl)methylamino]-2-hydroxypropanesulfonic Acid ("TAPSO"), or any suitable salts thereof. Typically, the amount of ampholyte present in an aqueous running buffer will be in the range of about 10 mM to about 100 mM, about 15 mM to about 75 mM, about 25 mM to about 50 mM or about 40 mM to about 45 mM. The running buffer may optionally include an additional buffering agent such as tris, in addition to SDS and EDTA. An exemplary though non-limiting example of a running buffer well suited for use with the presently disclosed embodiments may include 25-100 mM MES, 25-100 mM Tris, about 0.05 to about 0.5 SDS and about 0.5 mM to about 2 mM EDTA.

This gel and buffer system also possesses improved stability of the gel matrix and stock solutions. Gels prepared according to this system can be stored under refrigeration for over a year without loss of performance due to acrylamide hydrolysis. Also, stock buffers and stock gel solutions without polymerization initiator can be stored for at least several weeks at room temperature with no loss of performance.

In an embodiment of this gel formulation, an electrophoresis gel is uniformly saturated with a gel buffer solution comprising a primary organic amine or substituted amine with a pKa near neutrality, and a submolar amount of acid or ampholyte buffer as described above, so that the pH of the buffer is between about pH 6 and pH 8, preferably between about pH 6.5 to pH 7.5, and most preferably 6.5 to 7.0. The electrophoresis gel may be any agarose or polyacrylamide gel or a composite gel containing both agarose and polyacrylamide. Preferably, the electrophoresis gel comprises between 3% and 25% (% T) acrylamide polymerized using from about 1% to about 6% cross linker (% C). More preferably, this polyacrylamide gel is polymerized using from about 2% to about 5% crosslinker (% C). Preferably, the amine comprises Bis-Tris or N-(2-hydroxyethyl) morpholine, and most preferably, Bis-Tris. Suitable acids and zwitterionic compounds are tricine, bicine, N-(2-acetamido)-2-aminoethanesulfonic acid, 2-(N-morpholino)-2-hydroxypropanesulfonic acid, N-tris-(hydroxymethyl)-2-ethanesulfonic acid, N-2-hydroxyethyl-piperazine-N-2-ethanesulfonic acid, N,N-bis-(hydroxyethyl)-2-aminoethanesulfonic acid, and 3-(N-tris-(hydroxymethyl) methylamino)-2-hydroxypropanesulfonic acid.

In a gel and buffer system, current increases and migration rates decline as the performance of the gels decline due to hydrolysis of the polyacrylamide matrix. Any breakdown in a neutral substance present at a large concentration, which produces a charged species, will tend to disrupt the electrophoresis. This disruption arises from the extra current produced, which in turn increases joule eating without aiding the separation. In addition, a discontinuity arises from the anionic and cationic hydrolysis products forming in the gel that are not present in the cathode and anode buffers. Hydrolysis of gel buffer species or additives takes place independently from the gel matrix composition. The decrease in migration rate may be attributed to higher fixed charge in the gel caused by alkaline-catalyzed hydrolysis of the gel's polyacrylamide. The fixed charge leads to significant counter-flow of water, which can retard a macromolecule's migration rate. It has been found that problems of gel instability producing lower resolution, increased current, decreased migration rates can be solved with gels buffered near neutrality and with buffer substances having a pKa near neutrality. Such buffering systems improve the performance of fresh or pre-cast polyacrylamide gels, and fresh or pre-cast gels containing alkaline-labile materials, such as urea or formamide, even when the gels are made with base-stable polymers.

Without being bound by any one particular theory or mechanism of action, it has been determined that it is advantageous to use different buffer substances in the gel versus the anode and cathode buffers. In some embodiments, the anionic substance used in the gel or the cathode buffer need not be present in the anode buffer since the anions do not migrate out of the anode buffer.

These buffer systems provide the benefits of a neutral pH gel during storage and running, the least cost, and the fastest run times.

A variety of methods for preparing the subject discontinuous electrophoresis gels are known to those having ordinary skill in the art, and any such methods may be employed to prepare an electrophoresis gel without limitation. Described below is one exemplary method that one skilled in the art may use to prepare a discontinuous electrophoresis gel. It will be readily understood however, that other methods of preparing discontinuous electrophoresis gels may be equally employed, without departing from the spirit and scope of the present embodiments.

In an embodiment, aqueous stock solutions of acrylamide and bis-acrylamide may be prepared. Optionally, a single stock solution of acrylamide and bis-acrylamide may be prepared. Additionally, separate aqueous stock solutions of sucrose, a gel amine, a gel ampholyte and a chloride containing acid may be prepared. Optionally, separate stock solutions of SDS and reducing agent may be prepared. Finally, stock solutions of ammonium persulfate (APS; typically 10 wt. %) and tetramethylethylenediamine (TEMED; typically between 4 wt. % to 10%) are prepared. Appropriate amounts of the various stock solutions may be combined such that the final composition has the desired concentration of each individual component, except for the APS and TEMED, and the volume adjusted with an appropriate diluent (e.g., water) such that the correct concentration of each constituent is present. At this time, the APS and TEMED are added so that polymerization of the acrylamide, and bis-acrylamide is initiated. The mixture may then be cast between to glass or plastic plates. The plates may be spaced from each other such that the space between the plates in which the gel is cast is between 2 mm to 0.5 mm apart. Additionally, the space between the plates will be sealed on at least three sides. Optionally, a thin layer of butanol or aqueous buffer may be applied over the surface of the polymerizing gel, to reduce surface tension of the polymerizing gel composition and ensure that the upper edge of the polymerized gel is substantially straight. After the polymerizing gel composition is cast between the plates, the gel composition is allowed to rest for an appropriate amount of time to achieve substantially complete polymerization of the acrylamide and bis-acrylamide monomers.

In some embodiments, a stacking gel solution may be separately prepared and cast over the polymerized resolving gel. The S:R ratio of the fully polymerized electrophoresis gel will typically be about 1:4 or about 1.9:7.5, though various other S:R ratios may also be employed as described above and exemplified below. After the stacking gel has been cast, but prior to the polymerization reaction proceeding to completion, one or more combs may be inserted into the aqueous polymerizing stacking gel composition, between the two glass or plastic combs, thereby defining a plurality of wells into which the sample may be added immediately prior to use. Alternatively, in embodiments where no stacking gel is used, the combs may be inserted into the polymerizing aqueous resolving gel mixture described above. Typically, though not necessarily, the combs may be kept in place until the electrophoresis gel is ready for use, after which time the comb is remove and the sample may be loaded into the well defined by the polymerized polyacrylamide gel matrix.

In some embodiments, the percentage of polyacrylamide may vary through the length of an electrophoresis gel. A variety of such gradient gels are widely known in the art, any of which may be adapted for use with the presently described formulations. Gradient gels may be from about 2% to about 30% polyacrylamide, from about 3% to about 27% polyacrylamide, from about 4% to about 20% polyacrylamide, or from about 5% to about 15% polyacrylamide. In some embodiments, gradient gels may be from about 3% to about 12% polyacrylamide, from about 3% to about 20% polyacrylamide, from about 3% to about 15% polyacrylamide, from about 4% to about 12% polyacrylamide, from about 4% to about 20% polyacrylamide, or from about 4% to about 15% polyacrylamide. Any methods suitable for preparing gradient polyacrylamide gels may be used to prepare gradient gels having the subject formulations without limitation. Such methods are widely known to one having ordinary skill in the art to which the present embodiment pertains. Such methods are disclosed in, e.g., U.S. Pat. Nos. 6,488,880; 6,267,579; 4,594,064; and 5,071,531. In an embodiment, a gradient gel may optionally include a stacking gel cast in accordance with the methods discussed above and incorporated herein.

In some embodiments, the electrophoretic gel systems and compositions may be packaged in air or water-tight packaging following the polymerization of the gels. The air or water-tight packaging may be specifically adapted to maximize moisture retention by the cast gel and to prevent dehydration of the gel, which may adversely affect the performance thereof. In an embodiment, each gel may be individually packaged in air or water-tight packaging and provided to a customer as part of a kit. In an embodiment a kit may include a plurality of such individually packaged electrophoretic gels. In an embodiment, a kit may include 2-100 individually packaged electrophoretic gels, 5-75 individually packaged electrophoretic gels, 10-50 individually packaged electrophoretic gels, 15-35 individually packaged electrophoretic gels, or 20-25 individually packaged electrophoretic gels. The sets of gels may themselves be packaged in a suitable container that is shipped to an end user and is suitable to store the individually packaged gels in an appropriate environment. Electrophoretic gels prepared in accordance with the presently described compositions and methods are storage stable for up to 6 month, up to 5 months, up to 4 months, up to 3 months, up to 2 months or up to 1 month at temperature ranges from about 1° C. to about 25° C., or from about 4° C. to about 22° C. In some embodiments, a kit containing a plurality of individually packaged electrophoretic separation gels may optionally be provided to a customer in combination with one or more appropriate aqueous running buffers. The aqueous running buffers may be provided at a ready-to-use concentration, or may alternatively be provided in a concentrated form that a user can dilute as need. The aqueous running buffer may be provided, for example at a 20× stock solution, a 15× stock solution, a 10× stock solution, a 5× stock solution or a 2× stock solution.

In an embodiment, an electrophoretic separation gel may be assembled into an appropriate tank system that facilitates the application of an electric field along the length of the gel. Such a tank system will be configured to ensure that the aqueous running buffer interacts with the gel and allows the voltage to be applied equally along the entire longitudinal axis of the gel as disclosed in detail above and incorporated herein.

The following examples are included to demonstrate some preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that one or more changes can be made in the specific embodiments which are disclosed and still obtain a like or similar result without departing from the spirit and scope of the embodiments set forth herein.

EXAMPLES

The following experiments were performed to determine the range of various constituents suitable for use in fastrunning gel formulations embodied herein. In particular, various combinations of gel buffer constituents and salts were assessed. Unless otherwise indicated, resolving polyacrylamide gels having the compositions defined below were 8% polyacrylamide and 4.4% bis-acrylamide cross-linker (8% T/4.4% C). Stacking gels having 4% polyacrylamide and 3.8% bis-acrylamide cross-linker (4% T/3.8% C) were hand-cast on top of the resolving gel. Unless otherwise stated, the ratio of stacking gel to resolving gel (S:R) was about 1:4, the thickness of the gels was about 1 mm, and the gels were hand-cast in mini gel cassettes.

The samples used to test various gel formulations described below consisted of one or more of the following: Mark12™, SeeBlue Plus2® Pre-stained marker, Novex® Sharp Pre-stained, and E. coli lysate (all obtained from Life Technologies Corporation, Carlsbad, Calif.), in the indicated lanes. Mark12™ was chosen due to its high salt concentration at high loads (10 µL) and its historical use as the standard of choice for qualifying NuPAGE® gels. Novex® Sharp Pre-stained standards were chosen to facilitate visual tracking of the 3.5 kDa band corresponding to Insulin, chain B, so that completion of the gel run can be easily monitored. SeeBlue Plus2® was chosen because it is known that migration of the 19-22 kDa rhodamine-labeled myoglobin band can vary with amount of voltage. For example, when SeeBlue Plus2® protein standards are run on a NuPAGE® gel in turbo mode (i.e., 250 V), the myoglobin band runs at a lower apparent molecular weight than if the gels were run in normal mode (i.e., 200 V). E. coli lysate was chosen to observe migration of a complex protein sample.

Example 1

The first test gel formulation examined was an 8% SDS-PAGE resolving gel having the following composition: 100 mM Bis-Tris, 75 mM Tricine, 4 vol. % sucrose, and 20 mM BES. The stacking gel had the following composition: 357 mM Bis-Tris and 210 mM Chloride, pH 6.5 cast on top of the resolving gel. The S:R ratio of the gel was 1:4.

Five (5) µL of Mark12™ protein marker with Ponceau S tracking dye was loaded in each lane of the gel and the gel was run at 300 V for 15 minutes in NuPAGE® MES SDS Running Buffer (Invitrogen Corp., Carlsbad, Calif.). Completion of the gel run was determined based on the migration of Ponceau S tracking dye added separately to each sample to the bottom of the gel. At the completion of the run, the gel was stained with Coomassie® G-250 using SimplyBlue™ SafeStain (from Invitrogen Corp, Carlsbad, Calif.).

FIG. 1 shows the migration pattern of the marker bands resulting from this gel formulation. The 3.5 kDa insulin B band (indicated in FIG. 1) only migrated about ⅔ of the length of the gel. This indicates that the (Ponceau S) tracking dye migrated faster than the lower molecular weight proteins. Additionally, the bands migrating faster than the 55.4 kDa glutamic dehydrogenase band (indicated in FIG. 1) appear more diffuse than those migrating slower than the 55.4 kDa band, and the outer edges of the 6 kDa aprotinin band and the 3.5 kDa insulin B band are curved toward the bottom of the gel. Thus, while the gel run time of 15 minutes is improved, resolution of the bands using this gel formulation was not optimal.

Example 2

An SDS-PAGE test gel was cast essentially as described in Example 1, except that the S:R ratio was changed to 41:59 in an attempt to improve the stacking and separation of bands migrating higher than the 55.4 kDa glutamic dehydrogenase band. Five (5) µL of Mark12™ protein marker was loaded in each lane of the gel and the gel was run at 300 V for 16 minutes in MES SDS Running Buffer. Completion of the gel run was determined based on the migration the Ponceau S tracking dye to the bottom of the gel and the gel was stained with SimplyBlue™ SafeStain as above.

The resulting gel (FIG. 2) shows the migration pattern of the marker bands resulting from this gel formulation. The 3.5 kDa Insulin B band migrated the entire length of the gel, although an additional 1 min of run time was required. The 200 kDa myosin band in the outermost lanes (i.e., lanes 1, 2, 9 and 10; indicated by the asterisk) was more diffuse than the corresponding band seen in lanes 3-8. Additionally, bands migrating faster that the 55.4 kDa glutamic dehydrogenase band (indicated in FIG. 2) were more diffuse than those migrating slower than the 55.4 kDa band, and the outer edges of the 6 kDa aprotinin band and the 3.5 kDa insulin B band were curved toward the bottom of the gel.

Example 3

An SDS-PAGE test gel was cast essentially as described in Example 2, with the following changes: the 8% (8% T/4.4% C) resolving gel was made using 100 mM Bis-Tris and 100 mM Tricine. The 4% (4% T/3.8% C) stacking gel cast over the resolving gel had a pH of 6.1 and was made using 357 mM Bis-Tris and 150 mM sulfuric acid. In this example, sulfuric acid was used in order to provide a leading ion ($SO_4^{-2}$) that migrated slower than $Cl^-$. The S:R ratio of the gel was 41:59. Five (5) µL of Mark12™ protein marker was loaded in each lane of the gel and the gel was run at 300 V for 18 minutes in MES SDS Running Buffer. Completion of the gel run was determined based on the migration of the Ponceau S tracking dye to the bottom of the gel after which the gel was stained with SimplyBlue™ SafeStain as above.

Figure 3:
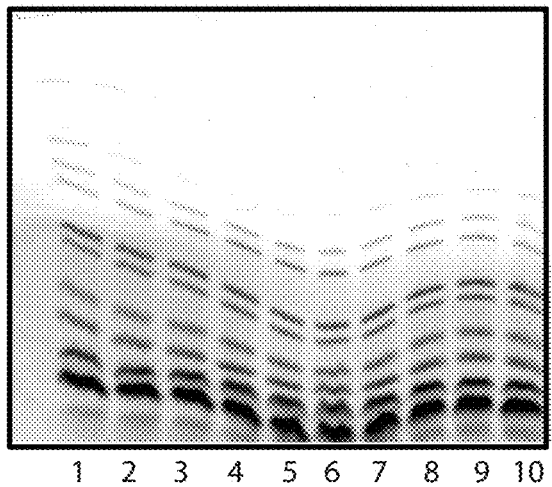
FIG. 3 shows a representative test gel according to one embodiment, in which a 4% stacking gel having 357 mM Bis-Tris, 150 mM $H_2SO_4$, pH 6.1 is cast over an 8% resolving gel (S:R=41:59) having 100 mM Bis-Tris, 100 mM Tricine, and 4 wt. % sucrose. 5 µl of Mark12™ protein marker was resolved at 300 V for 18 min in MES buffer, and the gel was stained with SimplyBlue™ SafeStain.

FIG. 3 shows the migration pattern of the marker bands resulting from this gel formulation. As shown, the use of sulfuric acid in the stacking gel yielded unsatisfactory results and appeared to overwhelm the buffering capability and resolution of the MES buffer.

Example 4

Two identical 8% SDS-PAGE resolving gels were cast essentially as described in Example 2, except that the amount of Bis-Tris in each gel was reduced to 178 mM, the chloride was reduced to 105 mM, and tricine was absent. A 4% stacking gel comprising 178 mM Bis-Tris, 105 mM chloride having pH 6.5 was cast on top of the each resolving gel. The S:R ratio of the gel was 1:3.

Five (5) µl Mark12™ protein marker was loaded in lanes 1-3, 5, 7, 9 and 10 of each gel, 5 µl SeeBlue Plus2® Pre-Stained Protein Standard was loaded in lane 4, 10 µg E. coli lysate was loaded in lane 6, and 5 µl Novex® Sharp Pre-Stained Protein Standard was loaded in lane 8. One of the gels (shown in FIG. 4A) was run in MES SDS Running Buffer at 300 V for 13 minutes, and the second gel (shown in FIG. 4B) was run in MES running buffer at 350 V for 10 minutes. Completion of the gel run was determined by visualizing migration of the pre-stained 3.5 kDa band in lane 8. The gel was stained with SimplyBlue™ SafeStain as above.

Figure 2:
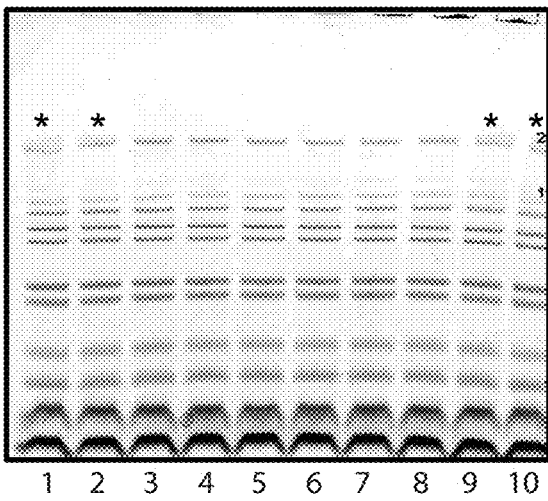
FIG. 2 shows a representative test gel according to one embodiment, in which a 4% stacking gel having 357 mM Bis-Tris, 210 mM Cl⁻, pH 6.5 is cast over an 8% resolving gel (S:R=41:59) having 100 mM Bis-Tris, 75 mM Tricine, 4 wt. % sucrose and 20 mM BES. 5 µl of Mark12™ protein marker was resolved at 300 V for 16 min in MES SDS running buffer, and the gel was stained with SimplyBlue™ SafeStain.

The 3.5 kDa insulin B band seen in FIGS. 4A and 4B shows better migration characteristics than the gels depicted in FIGS. 1-3, although the bands are broader than the bands in lanes 4 and 8. Overall, for the gel shown in FIG. 4B that was run at 350 V, the bands corresponding to the lower molecular weights were broader than the corresponding bands in the gel shown in FIG. 4A that was run at 300 V. Additionally, some band splitting is seen with the bands in the 66-6 kDa range in the gel run at 350 V (FIG. 4B).

Example 5

An 8% SDS-PAGE resolving gel was cast essentially as described in Example 1, except that the concentration of Bis-Tris was increased to 228 mM, the concentration of chloride was adjusted to 140 mM, the concentration of tricine was reduced to 50 mM, BES was removed, and the pH of the resolving gel was 6.5. A 4% stacking gel comprising 228 mM Bis-Tris, 140 mM Cl⁻, 50 mM Tricine, and 0 wt. % sucrose was cast on top of the resolving gel. Five (5) µl Mark12™ protein marker was loaded in lanes 1, 2, 5-7, 9 and 10, 5 µl SeeBlue Plus2® Pre-Stained Protein Standard was loaded in lane 3, 10 µg E. coli lysate was loaded in lane 4, and 5 µl Novex® Sharp Pre-Stained Protein Standard was loaded in lane 8. The gel was run in MES SDS Running Buffer at 300 V for 13 minutes. Completion of the gel run was determined by visualizing migration of the 3.5 kDa band in lane 8. The gel, shown in FIG. 5, was stained with SimplyBlue™ SafeStain as above. Broadening of the lower molecular weight bands was reduced, and band sharpness was improved by the addition of 50 to 100 mM tricine and 120-160 mM chloride.

Example 6

Figure 6D:
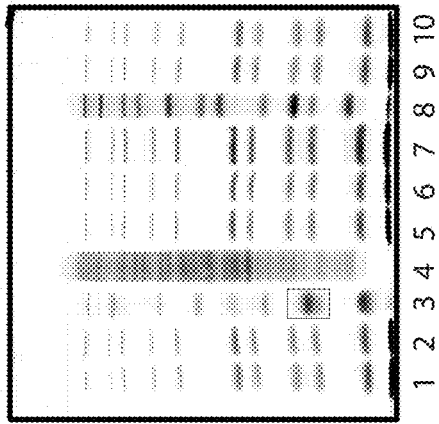
FIG. 6D shows a representative test gel according to one embodiment, in which a 4% stacking gel having 228 mM Bis-Tris, 140 mM Cl⁻, 50 mM Tricine, 0% sucrose, pH 6.5 is cast over an 8% resolving gel (S:R=1:4) having 228 mM Bis-Tris, 140 mM Cl⁻, 50 mM Tricine, 4% sucrose, and no BES, where 5 μl Mark12™ protein marker is loaded in lanes 1, 2, 5-6, 9 and 10, 5 μl SeeBlue Plus2® Pre-Stained Protein Standard is loaded in lane 3, 10 μg *E. coli* lysate is loaded in lane 4, 10 μl Mark12™ protein marker loaded in lane 7, and 5 μl Novex® Sharp Pre-Stained Protein Standard is loaded in lane 8, and the gel is run in MES SDS Running Buffer at 250 V for 19 minutes and stained with SimplyBlue™ SafeStain.
Figure 6E:
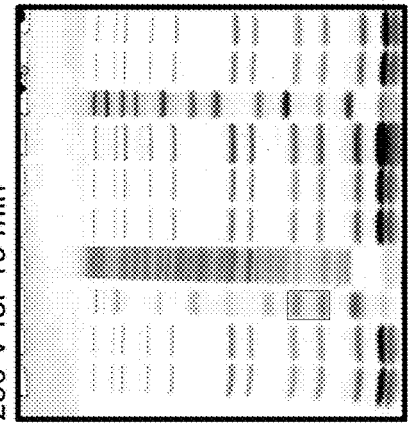
FIG. 6E shows a representative NuPAGE® Novex 8% Bis-Tris gel with 5 μl Mark12™ protein marker loaded in lanes 1, 2, 5-6, 9 and 10, 5 μl SeeBlue Plus2® Pre-Stained Protein Standard loaded in lane 3, 10 μg *E. coli* lysate loaded in lane 4, 10 μl Mark12™ protein marker loaded in lane 7, and 5 μl Novex® Sharp Pre-Stained Protein Standard loaded in lane 8, run in MES SDS Running Buffer at 300 V for 16 minutes and stained with SimplyBlue™ SafeStain.
Figure 6F:
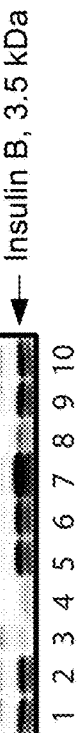
FIG. 6F shows a representative test gel according to one embodiment, in which a 4% stacking gel having 228 mM Bis-Tris, 140 mM Cl⁻, 50 mM Tricine, 0% sucrose, pH 6.5 is cast over an 8% resolving gel (S:R=1:4) having 228 mM Bis-Tris, 140 mM Cl⁻, 50 mM Tricine, 4% sucrose, and no BES, where 5 μl Mark12™ protein marker is loaded in lanes 1, 2, 5-6, 9 and 10, 5 μl SeeBlue Plus2® Pre-Stained Protein Standard is loaded in lane 3, 10 μg *E. coli* lysate is loaded in lane 4, 10 μl Mark12™ protein marker loaded in lane 7, and 5 μl Novex® Sharp Pre-Stained Protein Standard is loaded in lane 8, and the gel is run in MES SDS Running Buffer at 300 V for 16 minutes and stained with SimplyBlue™ SafeStain.
Figure 7A:
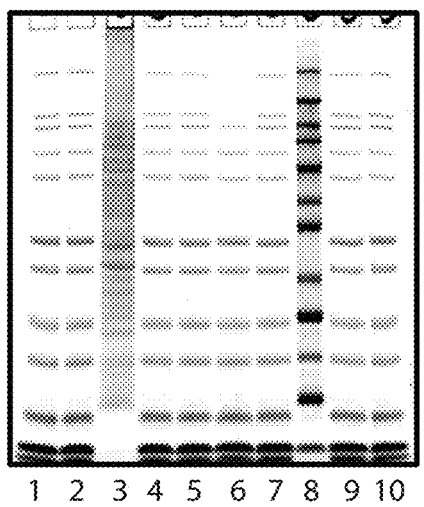
FIG. 7A shows a representative test gel according to one embodiment, in which a 4% stacking gel having 228 mM Bis-Tris, 140 mM Cl⁻, 50 mM Tricine, 0% sucrose, pH 6.5 was cast over an 8% resolving gel (S:R=1:4) having 228 mM Bis-Tris, 140 mM Cl⁻, 50 mM Tricine, 1.5% sucrose, and no BES, where 5 μl Mark12M protein marker was loaded in lanes 1, 2, 4-7, 9 and 10, 10 μg *E. coli* lysate was loaded in lane 3, and 5 μl Novex® Sharp Pre-Stained Protein Standard was loaded in lane 8, the gel was run at 300 V for 14 min in MES SDS running buffer and the gel was stained with SimplyBlue™ SafeStain.
Figure 7B:
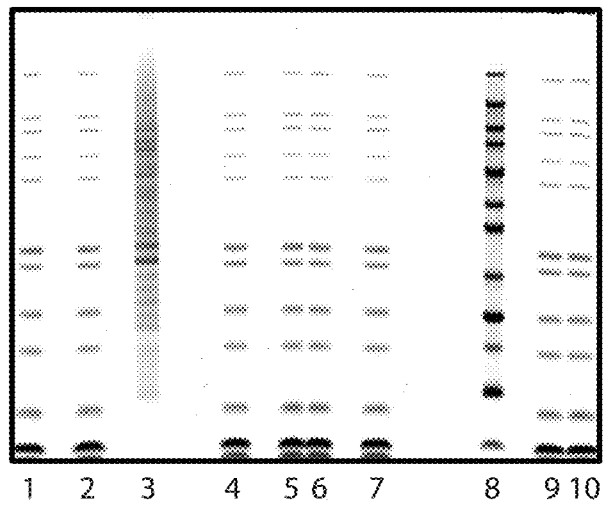
FIG. 7B shows a representative image of a 20 well NuPAGE® Novex 8% Bis-Tris gel, where lanes 1, 3, 8, 10, 11, 13, 18 and 19 were loaded with 5 μl Mark12™ protein marker, lane 5 was loaded with 10 μg *E. coli* lysate and lane 16 was loaded with 10 μl Novex® Sharp Pre-Stained Protein Standard, the gels was run at 200 V for 35 minutes in MES buffer and stained with SimplyBlue™ SafeStain.
Figure 7C:
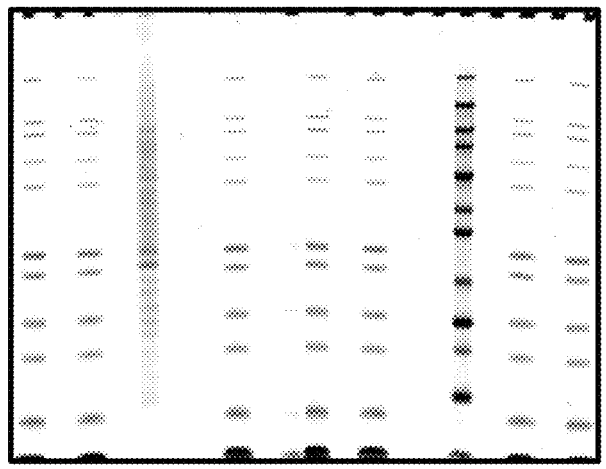
FIG. 7C shows a representative image of a 20 well NuPAGE® Novex 8% Bis-Tris gel, where lanes 1, 3, 8, 10, 11, 13, 18 and 19 were loaded with 5 μl Mark12™ protein marker, lane 5 was loaded with 10 μg *E. coli* lysate and lane 16 was loaded with 10 μl Novex® Sharp Pre-Stained Protein Standard, the gels was run at 250 V for 22 minutes in MES buffer and stained with SimplyBlue™ SafeStain.
Figure 7D:
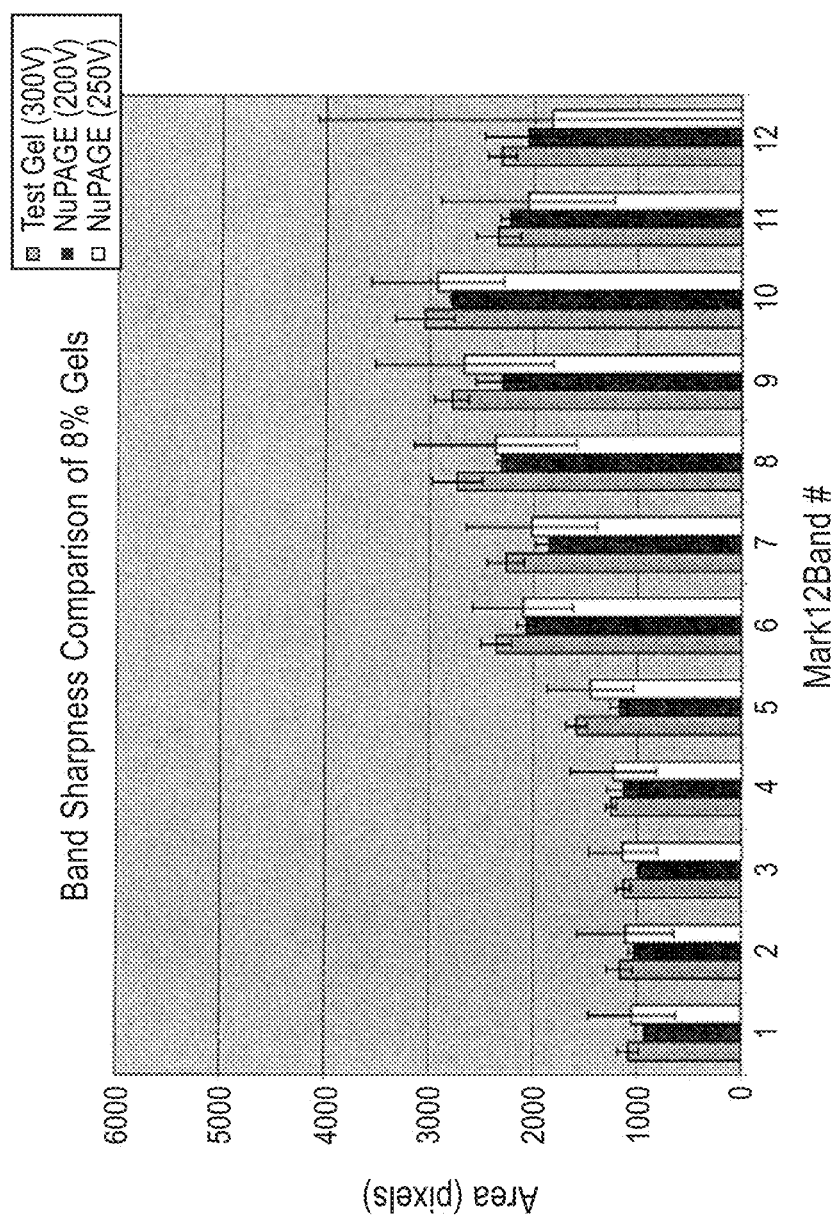
FIG. 7D is a bar graph indicating the relative sharpness of each individual band (measured by pixel area) of the Mark12™ protein marker set that was averaged over 7 independent experiments using the gel formulation described in FIG. 7A (grey bars), FIG. 7B (dark bars) and FIG. 7C (white bars). The X-axis indicates the band number, with band number 1 being the 200 kDa Mark12™ band and band 12 being the 2.5 kDa band.
Figure 7E:
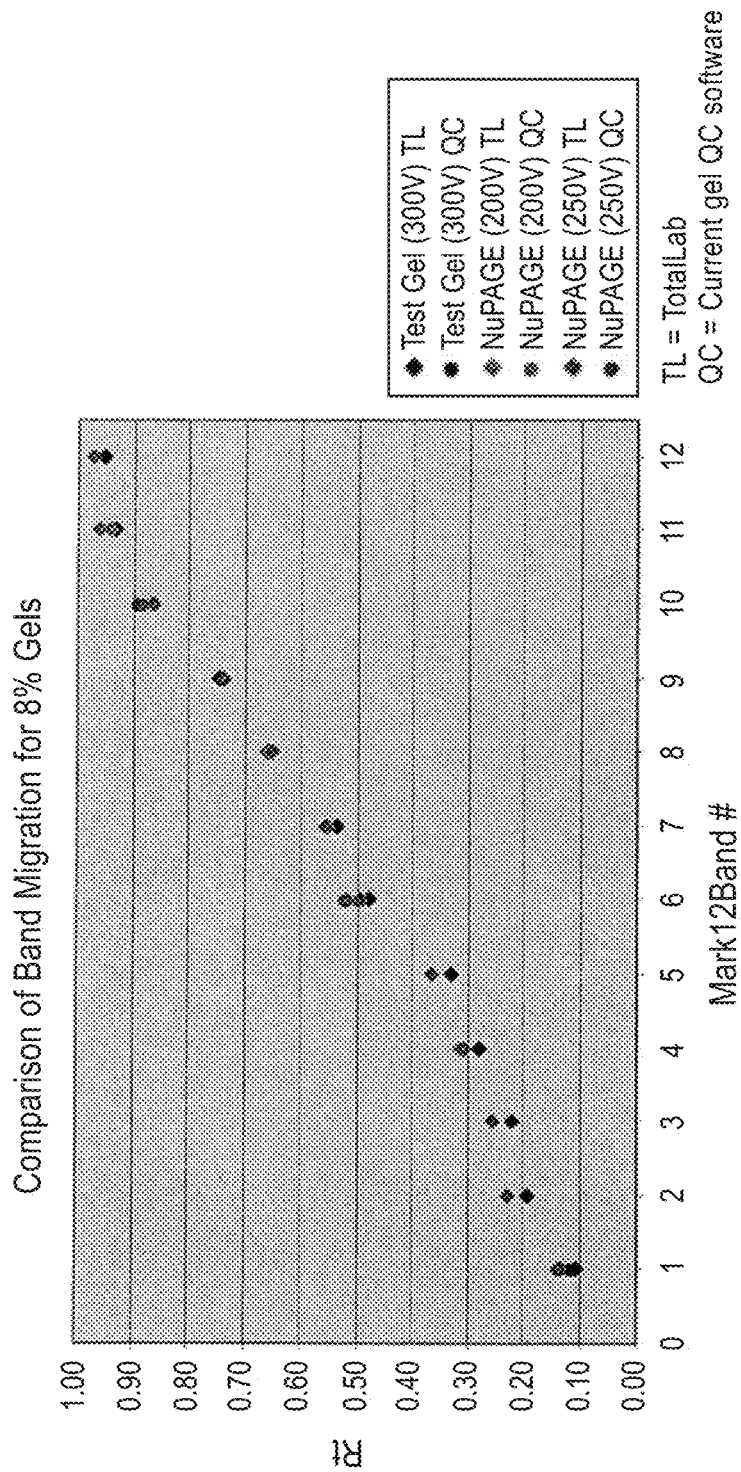
FIG. 7E is a graph depicting the average $R_f$ value obtained for each gel formulation described in FIG. 7A, FIG. 7B and FIG. 7C using either NonLinear Dynamics TOTALLAB™ v2003.02 software or QC Software as indicated.

FIG. 6 demonstrates the differences in electrophoresis characteristics between a commercially available SDS-PAGE gel formulation (NuPAGE® Novex 8% Bis-Tris Midi gels; FIGS. 6A, 6C and 6E) and the test gel formulation described in Example 5; namely, an 8% SDS-PAGE resolving gel having 228 mM Bis-Tris, 140 mM chloride and 50 mM tricine with 4% sucrose, and a 4% stacking gel with the same buffer composition and no sucrose, where the S:R ratio was 1.9:5.6 (indicated Test Gel in FIGS. 6B, 6D and 6F). The following samples were prepared and loaded on each of the gels: lanes 1, 2, 5, 6, 9 and 10 contained 5 µl Mark12™ protein marker, lane 7 contained 10 µl Mark12™ protein marker, lane 3 contained 5 µl SeeBlue Plus2® Pre-Stained Protein Standard, lane 4 contained 10 µg E. coli extract, and lane 8 contained 5 µl Novex® Sharp Pre-Stained Protein Standard. The NuPAGE® Novex 8% Bis-Tris gel and the test gel formulation were run in MES SDS Running Buffer at 200 V for 32 minutes and 29 minutes, respectively (FIGS. 6A and 6B); at 250 V for 20 minutes and 19 minutes, respectively (FIGS. 6C and 6D); and at 300 V for 16 minutes and 13 minutes, respectively (FIGS. 6E and 6F). After completion of the gel run, the gels were stained with SimplyBlue™ SafeStain as described above.

At 250V and 300V (FIGS. 6C-6F), the lower molecular weight insulin B bands (indicated by arrows) showed sharper resolution and shorter run times for the test gel formulation (FIGS. 6D and 6F) than in NuPAGE® Novex 8% Bis-Tris (FIGS. 6C and 6E). Additionally, at all voltages tested, the 14 and 17 kDa bands of the SeeBlue Plus2® Pre-Stained Protein Standard showed better resolution and separation in the test gel formulation (FIGS. 6B, 6D and 6F, lane 3, boxed area) than in the NuPAGE® Novex 8% Bis-Tris (FIGS. 6A, 6C and 6E, lane 3, boxed area).

Example 7

For the following experiments, test SDS-PAGE gels were cast essentially as described in Examples 5 and 6, except as noted below. For each set of experimental conditions, a total of 7 test SDS-PAGE gels were cast. The test SDS-PAGE formulations were run at 300 V for the indicated time. In each experiment, two (2) NuPAGE® Novex gels were tested for each of the indicated conditions (200 V or 250V). All gels were run in MES SDS Running Buffer for the indicated amount of time and at the indicated voltage. At the end of the run, each gel was stained with SimplyBlue™ SafeStain and imaged. The sharpness of each band was determined using TOTALLAB™ software (Nonlinear Dynamics Ltd, Durham, N.C.). Band sharpness was determined by measuring the area of each band and dividing the area by the width of each well (well width held constant 10 wells/gel). The migration of each band (determined by its $R_f$ value) was determined using TOTALLAB™ software and QC software.

In FIG. 7, 8% SDS-PAGE test gels as described in Example 6 were cast and compared with NuPAGE® Novex 8% Bis-Tris formulation. FIG. 7A shows a representative image obtained of a test SDS-PAGE gel run at 300 V for 14 minutes in MES buffer, where lanes 1, 2, 4-7, 9 and 10 were loaded with 5 µl Mark12™ protein marker, lane 3 was loaded with 10 µg E. coli lysate, and lane 8 was loaded with 10 µl Novex® Sharp Pre-Stained Protein Standard. FIG. 7B shows a representative image of a 20 well NuPAGE® Novex 8% Bis-Tris run at 200 V for 35 minutes in MES buffer, where lanes 1, 3, 8, 10, 11, 13, 18 and 19 were loaded with 5 µl Mark12™ protein marker, lane 5 was loaded with 10 µg E. coli lysate and lane 16 was loaded with 10 µl Novex® Sharp Pre-Stained Protein Standard. FIG. 7C shows a representative image of an identical gel described in FIG. 7B, except that the gel was run in MES SDS Running Buffer at 250 V for 22 minutes. FIG. 7D is a bar graph summarizing the relative sharpness of each individual band (measured by pixel area) of the Mark12™ protein marker that was obtained for each experimental condition. Test gel formulation run at 300V is shown as grey bars, NuPAGE® Novex 8% Bis-Tris gel run at 200 V is shown as black bars, and NuPAGE® Novex 8% Bis-Tris run at 250V using the Turbo protocol is shown as white bars. The x-axis indicates which of the Mark12™ protein marker bands is being analyzed, and the y-axis indicates pixel area. FIG. 7E shows the average $R_f$ value obtained for each gel formulation using either NonLinear Dynamics TOTALLAB™ v2003.02 software or QC Software as indicated.

Figure 8A:
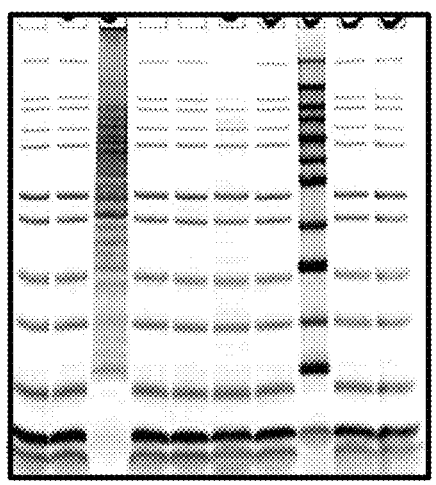
FIG. 8A shows a representative test gel according to one embodiment, in which a 4% stacking gel having 228 mM Bis-Tris, 140 mM Cl⁻, 50 mM Tricine, 0% sucrose, pH 6.5 is cast over a 10% resolving gel (S:R=1:4) having 228 mM Bis-Tris, 140 mM Cl⁻, 50 mM Tricine, 1.75% sucrose, and no BES, where 5 μl Mark12™ protein marker is loaded in lanes 1, 2, 4-7, 9 and 10, 10 μg *E. coli* lysate is loaded in lane 3, and 5 μl Novex® Sharp Pre-Stained Protein Standard is loaded in lane 8, the gel was run at 300 V for 16 min in MES SDS running buffer and the gel was stained with SimplyBlue™ SafeStain.
Figure 8B:
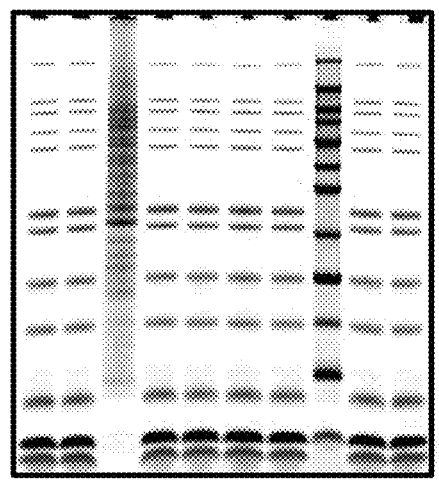
FIG. 8B shows a representative image of a 10 well NuPAGE® Novex 10% Bis-Tris gel, where 5 μl Mark12™ protein marker is loaded in lanes 1, 2, 4-7, 9 and 10, 10 μg *E. coli* lysate is loaded in lane 3, and 5 μl Novex® Sharp Pre-Stained Protein Standard is loaded in lane 8, the gels was run at 200 V for 36 minutes in MES buffer and stained with SimplyBlue™ SafeStain.
Figure 8C:
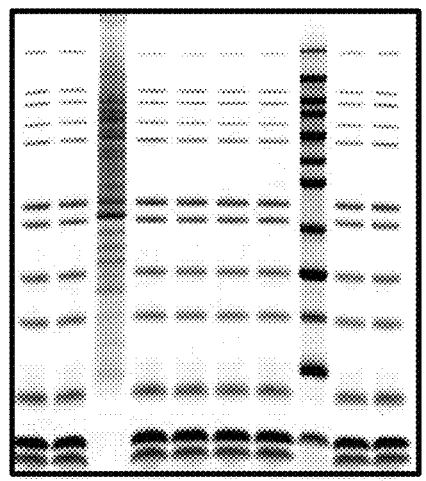
FIG. 8C shows a representative image of a 10 well NuPAGE® Novex 10% Bis-Tris gel, where 5 μl Mark12™ protein marker is loaded in lanes 1, 2, 4-7, 9 and 10, 10 μg *E. coli* lysate is loaded in lane 3, and 5 μl Novex® Sharp Pre-Stained Protein Standard is loaded in lane 8, the gels was run at 250 V for 24 minutes in MES buffer and stained with SimplyBlue™ SafeStain.
Figure 8D:
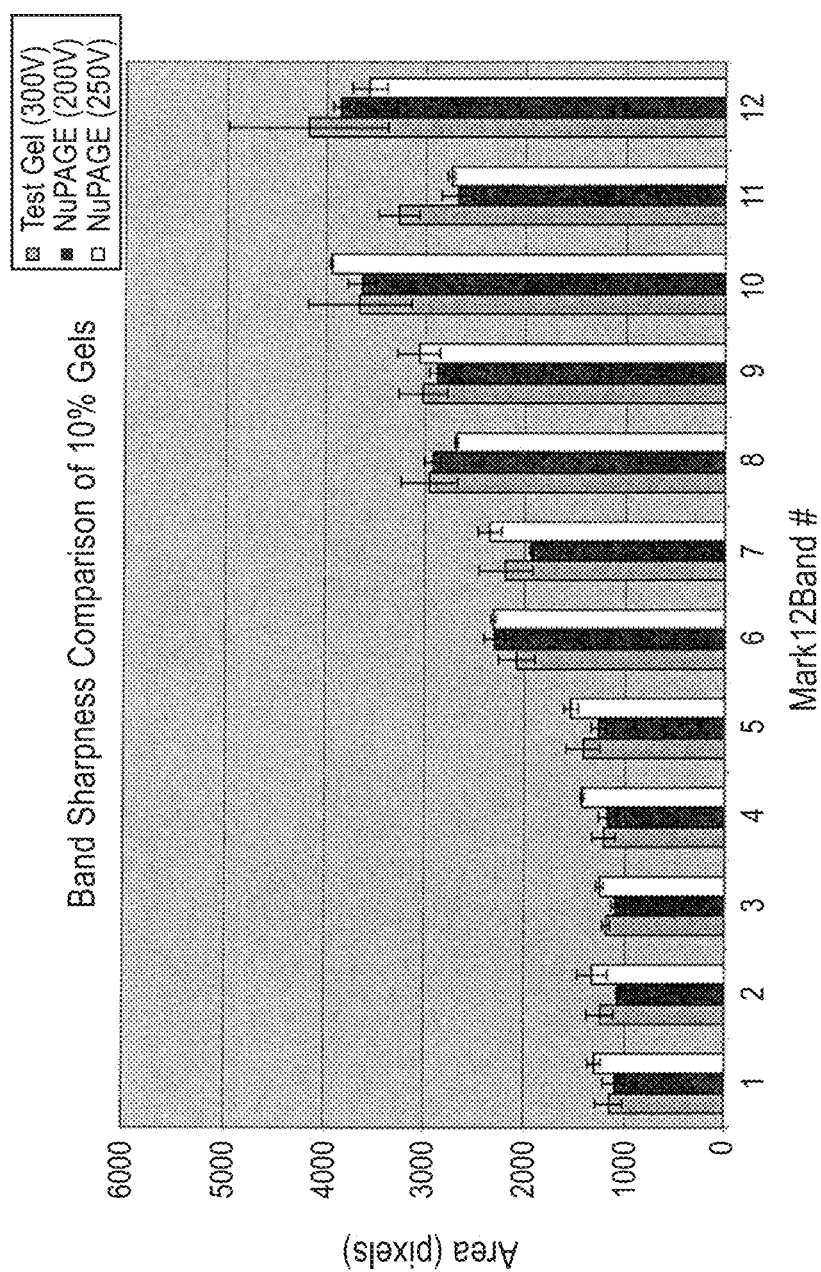
FIG. 8D is a bar graph indicating the relative sharpness of each individual band (measured by pixel area) of the Mark12™ protein marker set that was averaged over 7 independent experiments using the gel formulation described in FIG. 8A (grey bars), FIG. 8B (dark bars) and FIG. 8C (white bars). The X-axis indicates the band number, with band number 1 being the 200 kDa Mark12™ band and band 12 being the 2.5 kDa band.
Figure 8E:
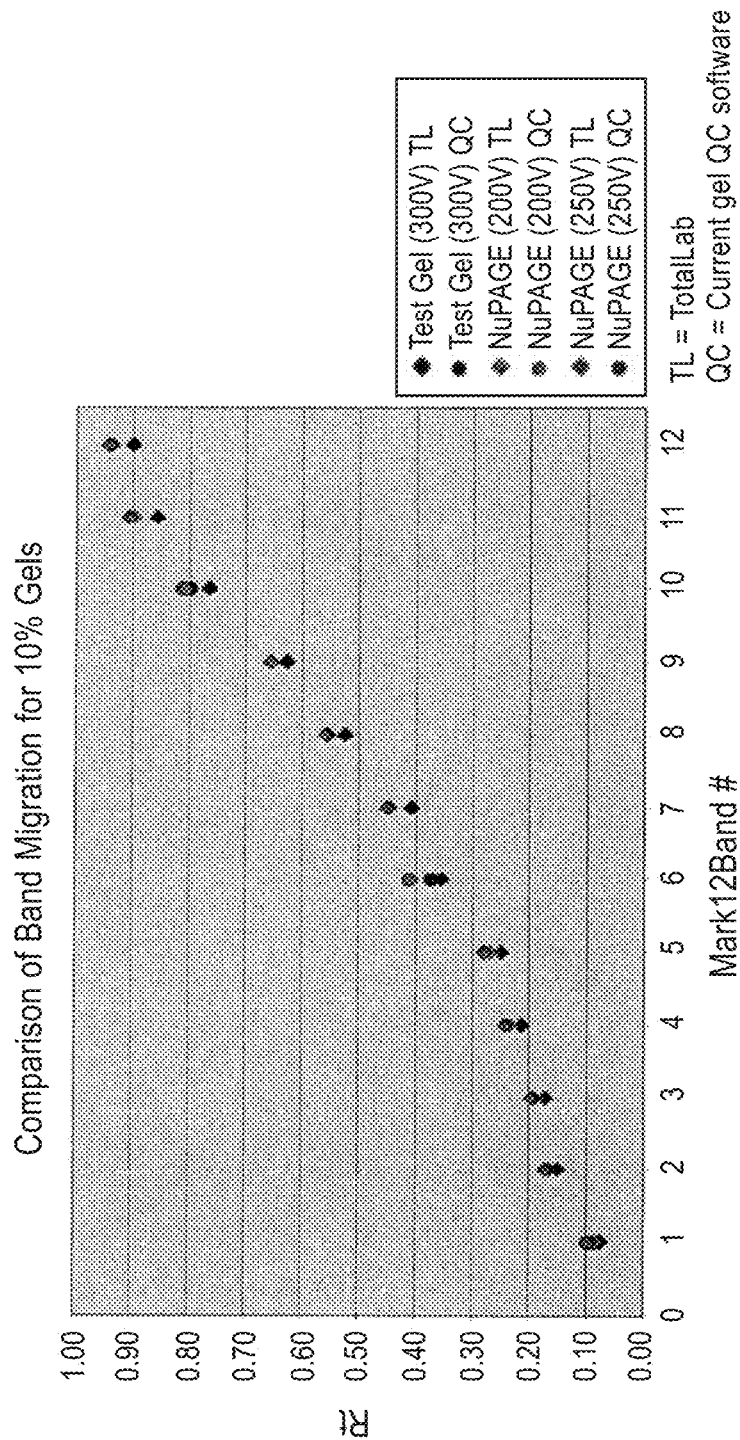
FIG. 8E is a graph depicting the average $R_f$ value obtained for each gel formulation described in FIG. 8A, FIG. 8B and FIG. 8C using either TOTALLAB™ software or QC Software as indicated.

The results shown in FIGS. 8A-8E were obtained essentially as described for FIGS. 7A-7E with the following exceptions. The polyacrylamide concentration in the test gels shown in FIG. 8A was increased to 10% and the gels were run in MES buffer at 300 V for 16 minutes. In FIGS. 8B and 8C, 10-well NuPAGE® Novex 10% Bis-Tris gels were used and the lanes were loaded as follows: lanes 1, 2, 5-6, 9 and 10 contained 5 µl Mark12™ protein marker, lane 3 contained 10 µg E. coli lysate, and lane 8 contained 10 µl Novex® Sharp Pre-Stained Protein Standard. In FIG. 8B, the gel was run at 200 V in MES buffer for 36 minutes, and in FIG. 8C, the gel was run in MES buffer at 250 V for 24 minutes. The analysis of the gels, shown in FIGS. 8D and 8E, was performed as described for FIGS. 7D and 7E.

Figure 9A:
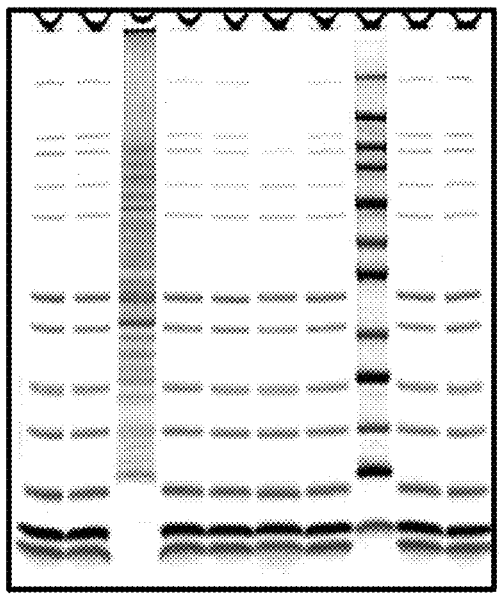
FIG. 9A shows a representative test gel according to one embodiment, in which a 4% stacking gel having 228 mM Bis-Tris, 140 mM Cl⁻, 50 mM Tricine, 0% sucrose, pH 6.5 is cast over a 4-12% gradient gel having 228 mM Bis-Tris, 140 mM Cl⁻, 50 mM Tricine, 1.5-2% sucrose, and no BES, where 5 µl Mark12™ protein marker is loaded in lanes 1, 2, 4-7, 9 and 10, 10 µg E. coli lysate is loaded in lane 3, and 5 µl Novex® Sharp Pre-Stained Protein Standard is loaded in lane 8, the gel was run at 300 V for 17 min in MES SDS running buffer and the gel was stained with SimplyBlue™ SafeStain.
Figure 9B:
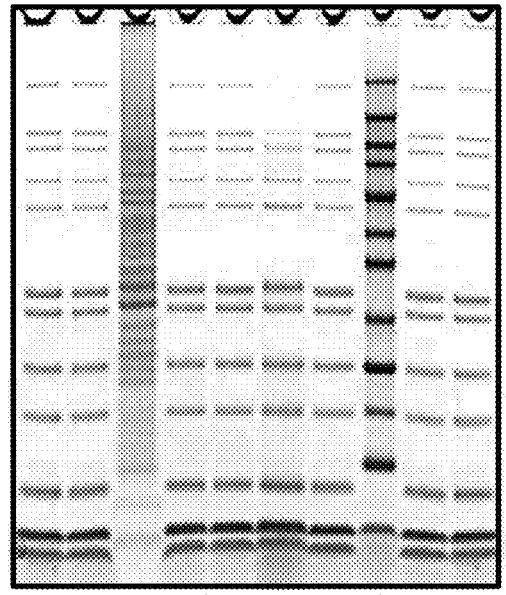
FIG. 9B shows a representative image of a 10 well NuPAGE® Novex 4-12% Bis-Tris gel, where 5 µl Mark12™ protein marker is loaded in lanes 1, 2, 4-7, 9 and 10, 10 µg E. coli lysate is loaded in lane 3, and 5 µl Novex® Sharp Pre-Stained Protein Standard is loaded in lane 8, the gels was run at 200 V for 37 minutes in MES buffer and stained with SimplyBlue™ SafeStain.
Figure 9C:
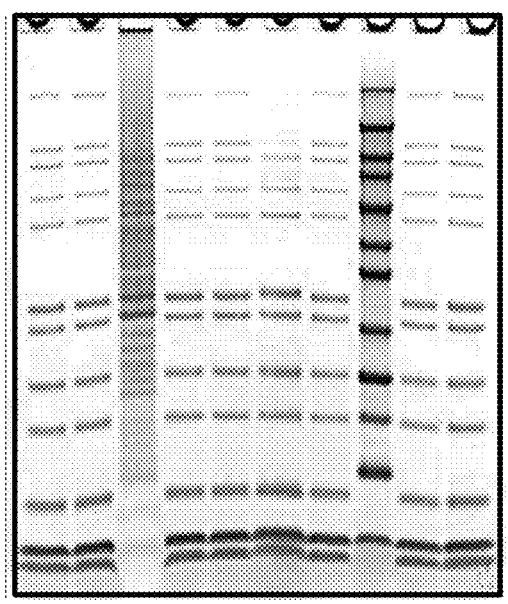
FIG. 9C shows a representative image of a 10 well NuPAGE® Novex 4-12% Bis-Tris gel, where 5 µl Mark12™ protein marker is loaded in lanes 1, 2, 4-7, 9 and 10, 10 µg E. coli lysate is loaded in lane 3, and 5 µl Novex® Sharp Pre-Stained Protein Standard is loaded in lane 8, the gels was run at 250 V for 25 minutes in MES buffer and stained with SimplyBlue™ SafeStain.
Figure 9D:
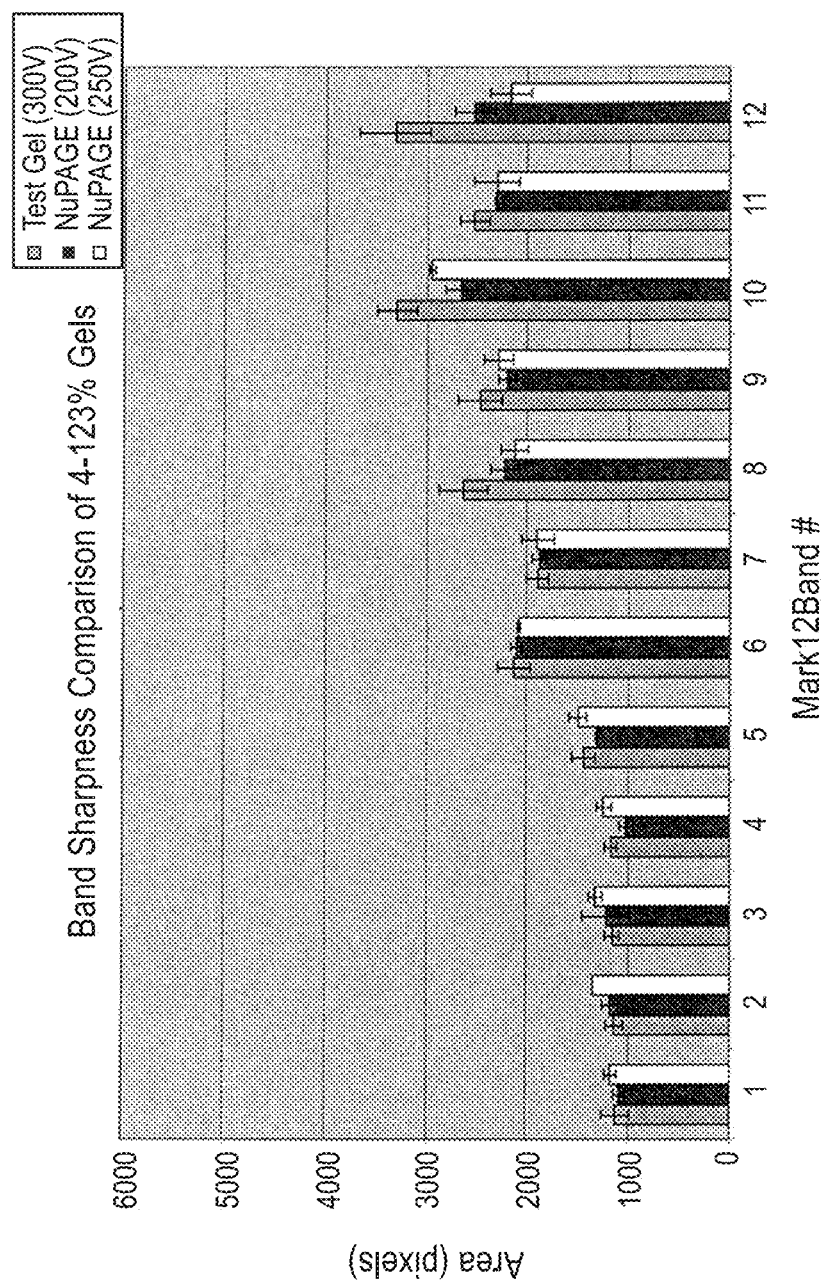
FIG. 9D is a bar graph indicating the relative sharpness of each individual band (measured by pixel area) of the Mark12™ protein marker set that was averaged over 7 independent experiments using the gel formulation described in FIG. 9A (grey bars), FIG. 9B (dark bars) and FIG. 9C (white bars). The X-axis indicates the band number, with band number 1 being the 200 kDa Mark12™ band and band 12 being the 2.5 kDa band.
Figure 9E:
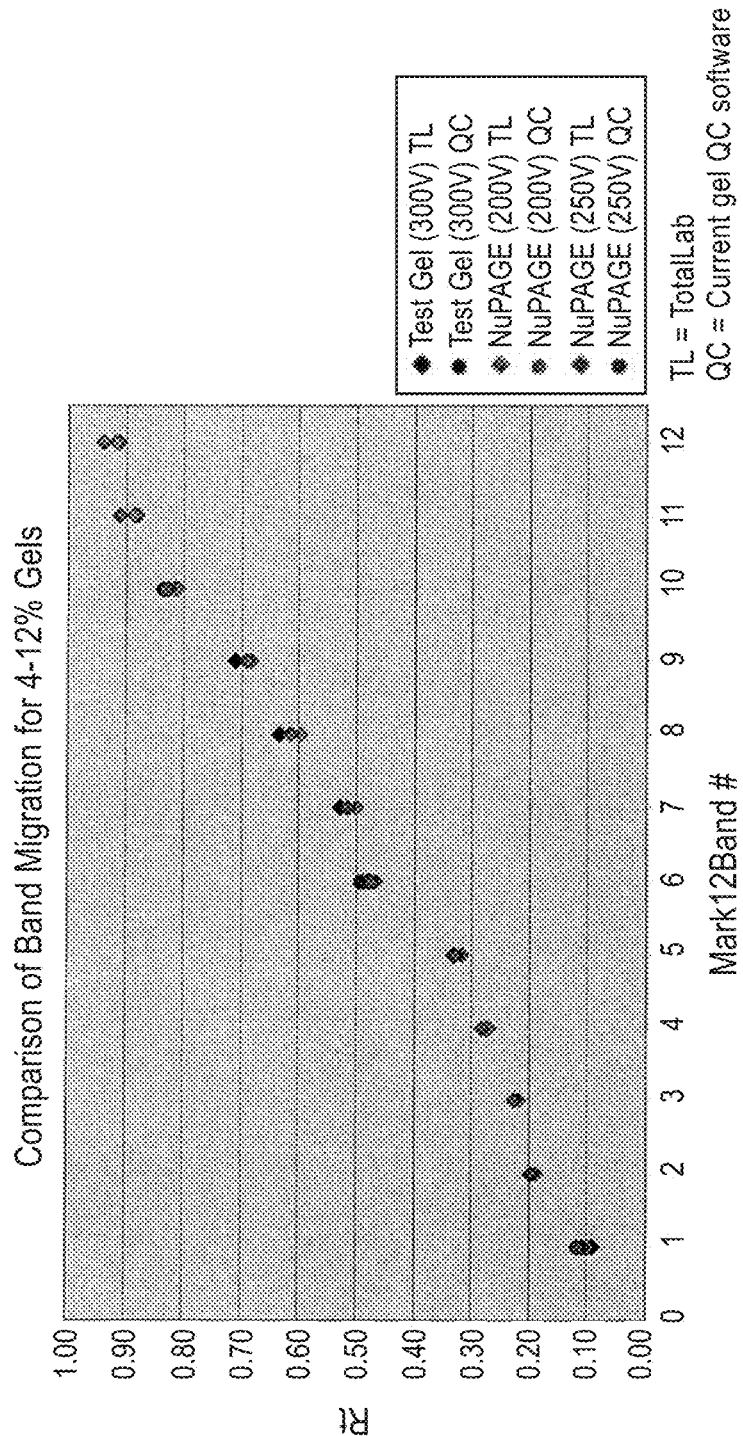
FIG. 9E is a graph depicting the average $R_f$ value obtained for each gel formulation described in FIG. 9A, FIG. 9B and FIG. 9C using either TOTALLAB™ software or QC Software as indicated.

The results shown in FIG. 9A-9E were obtained essentially as described for FIGS. 8A-8E with the following exceptions. The SDS-PAGE test gel shown in 9A was cast as a 4-12% polyacrylamide gradient gel run in MES buffer at 300V for 17 minutes. In FIGS. 9B and 9C, 12-well NuPAGE® Novex 4-12% Bis-Tris gels were used and the lanes were loaded as described for FIGS. 8B and 8C. In FIG. 9B, the gel was run at 200 V in MES buffer for 37 minutes, and in FIG. 9C, the gel was run in MES buffer at 250 V for 25 minutes. The analysis of the gels, shown in FIGS. 9D and 9E, was performed as described for FIGS. 7D and 7E.

Example 8

Figure 10A:
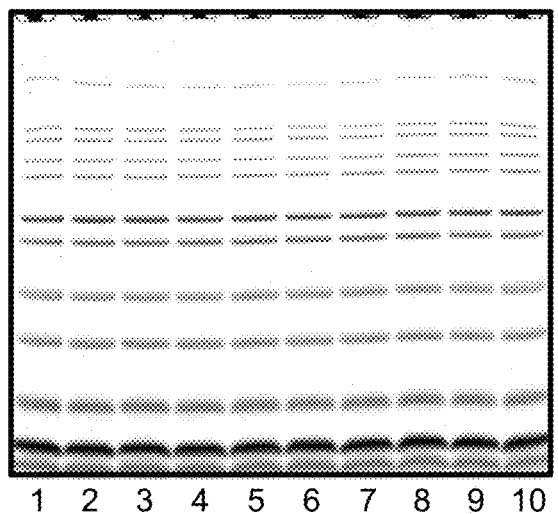
FIG. 10A shows a representative test gel according to one embodiment, in which a 4% stacking gel having 357 mM Bis-Tris, 210 mM Cl⁻, pH 6.5 is cast over a 12% resolving gel (S:R=1:4) having 228 mM Bis-Tris, 140 mM Cl⁻, 50 mM Tricine, 2% wt. % sucrose, and no BES, where 5 µl Mark12™ protein marker is loaded in lanes 1-10. The gel was run at 300 V for 15 min in MES SDS running buffer and the gel was stained with SimplyBlue™ SafeStain.
Figure 10B:
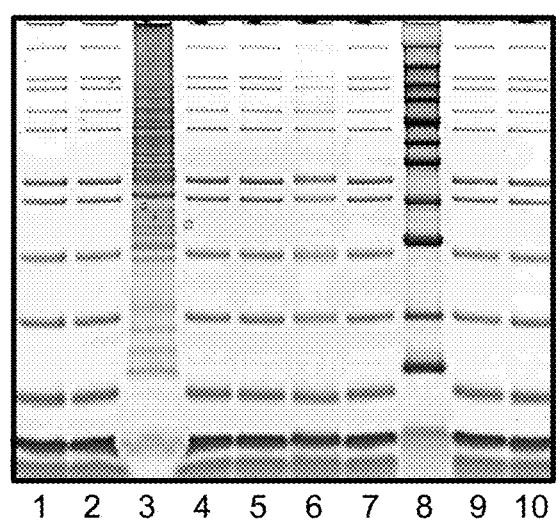
FIG. 10B shows a representative test gel according to one embodiment, in which a 4% stacking gel having 228 mM Bis-Tris, 140 mM Cl⁻, 50 mM Tricine, 0% sucrose, pH 6.5 is cast over a 12% resolving gel (S:R=1:4) having 228 mM Bis-Tris, 140 mM Cl⁻, 50 mM Tricine, 4% wt. % sucrose, and no BES, where 5 µl Mark12™ protein marker is loaded in lanes 1-10. The gel was run at 300 V for 26 min in MES SDS running buffer and the gel was stained with SimplyBlue™ SafeStain.
Figure 10C:
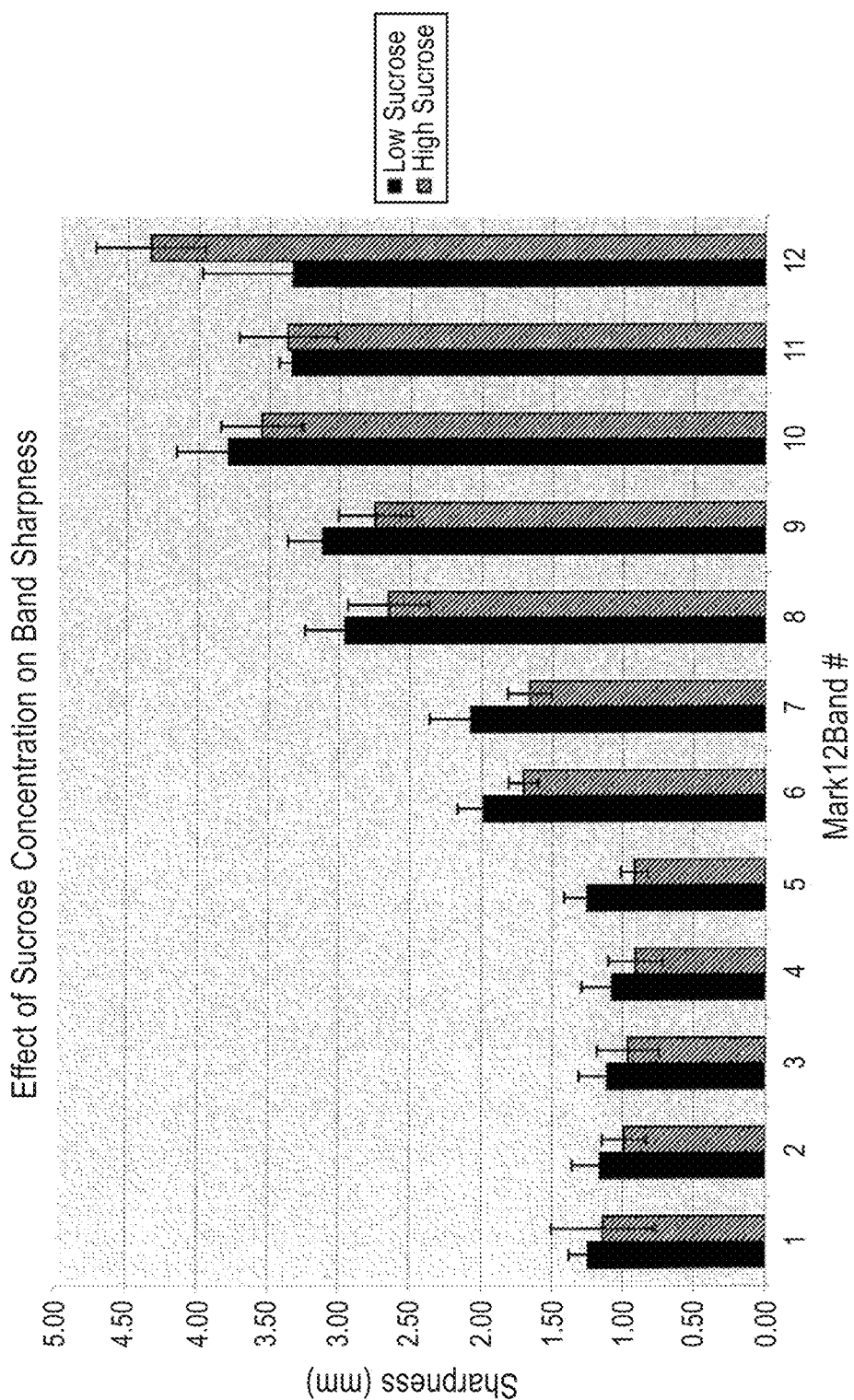
FIG. 10C is a bar graph indicating the relative sharpness of each individual band (measured by pixel area) of the Mark12™ protein marker set that was averaged over four independent experiments using the gel formulation described in FIG. 10A (black bars) and FIG. 10B (hatched bars) The X-axis indicates the band number, with band number 1 being the 200 kDa Mark12™ band and band 12 being the 2.5 kDa band.

For the following experiments shown in FIG. 10, two test SDS-PAGE gels were cast essentially as described in Examples 6 through 8, except that the sucrose concentration in the resolving gel shown in FIG. 10A was reduced to 2 wt. %, and the sucrose concentration in the resolving gel shown in FIG. 10B remained at 4 wt. %. In FIG. 10A, the gel was run at 300 V for 15 minutes. In FIG. 10B, the gel was run at 300 V for 26 minutes, FIG. 10C shows the relative band sharpness obtained for the gels shown in FIGS. 10A and 10B.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A discontinuous buffer electrophoretic system comprising:
    an electrophoretic separation gel, said electrophoretic separation gel comprising a gel buffer system, said buffer system comprising:
    a gel amine buffer selected from Bis-Tris, Bis-Tris propane, triethanolamine, and salts or combinations thereof at concentrations of about 200 mM to about 300 mM; and
    a gel ampholyte selected from tricine, bicine, HEPPS, glycinamide, TAPS and salts or combinations thereof at concentrations of from about 50 mM to about 100 mM; and
    an aqueous running buffer comprising a buffer ampholyte, wherein the gel ampholyte is different from the buffer ampholyte.

2. The discontinuous buffer electrophoretic system according to claim 1, wherein the separation gel comprises acrylamide, agarose, or acrylamide and agarose.

3. The discontinuous buffer electrophoretic system according to claim 1, wherein the separation gel comprises acrylamide.

4. The discontinuous buffer electrophoretic system according to claim 1, wherein the separation gel comprises between about 6 to about 25 wt. % acrylamide, between about 8 to about 20 wt. % acrylamide, or between about 8 to about 15 wt. % acrylamide.

5. The discontinuous buffer electrophoretic system according to claim 1, wherein the electrophoretic separation gel further comprises a stacking gel coupled to one end thereof.

6. The discontinuous buffer electrophoretic system according to claim 5, wherein the stacking gel comprises about 4 wt. % acrylamide.

7. The discontinuous buffer electrophoretic system according to claim 1, wherein the pK of the gel ampholyte is about 1.5 pK units greater than the pK of the gel amine.

8. The discontinuous buffer electrophoretic system according to claim 1, wherein the pK of the gel ampholyte is between about 7 to about 9, wherein the pK of the gel ampholyte is between about 8 to about 8.5, or wherein the pK of the gel ampholyte is between about 8.1 to about 8.3.

9. The discontinuous buffer electrophoretic system according to claim 1, wherein the pK of the gel amine buffer is in the range of about 5.5 to about 7.5.

10. The discontinuous buffer electrophoretic system according to claim 1, wherein the gel amine buffer is Bis-Tris.

11. The discontinuous buffer electrophoretic system according to claim 1, wherein the gel ampholyte is Tricine or Bicine.

12. The discontinuous buffer electrophoretic system according to either of claim 1, wherein the concentration of the gel ampholyte is about 50 mM or about 75 mM.

13. The discontinuous buffer electrophoretic system according to claim 1, wherein the pH of the gel buffer system is in the range of about 6 to about 8, wherein the pH of the gel buffer system is in the range of about 6.0 to about 7.5, wherein the pH of the gel buffer system is about 6.5, or wherein the pH of the gel buffer system is adjusted by the addition of an acid.

14. The discontinuous buffer electrophoretic system according to claim 13, wherein the acid is HCl.

15. The discontinuous buffer electrophoretic system according to claim 1, wherein the gel buffer system further includes a source of $Cl^-$ ions.

16. The discontinuous buffer electrophoretic system according to claim 15, wherein the gel buffer system further includes about 95 mM to about 170 mM $Cl^-$ ions or about 135 mM to about 145 mM $Cl^-$ ions.

17. The discontinuous buffer electrophoretic system according to claim 1, wherein the pK of the buffer ampholyte in the running buffer is less than the pK of the gel ampholyte.

18. The discontinuous buffer electrophoretic system according to claim 1, wherein the buffer ampholyte comprises IVIES, ADA, PIPES, ACES, BES, TES, HEPES, MOPS, CAPSO, DIPSO, POPSO, HEPPS, HEPPSO, salts thereof, or any combination thereof.

19. The discontinuous buffer electrophoretic system according to claim 1, wherein the electrophoretic separation gel further comprises sucrose, wherein the concentration of sucrose is less than about 5 wt, wherein the concentration of sucrose is less than about 3 wt. %, wherein the concentration of sucrose is less than about 2 wt. %, or wherein the concentration of sucrose is less than about 1.5 wt. %.

20. The discontinuous buffer electrophoretic system according to claim 1, further comprising SDS in at least the separating gel.

21. The discontinuous buffer electrophoretic system according to claim 20, further comprising SDS in the separating gel and the running buffer.

22. The discontinuous buffer electrophoretic system according to claim 1, wherein the separating gel is a slab gel.

23. The discontinuous buffer electrophoretic system according to claim 22, wherein the slab gel is between two glass or plastic plates.

24. A kit comprising:
one or more gel cassettes, wherein each of said one or more gel cassettes comprises a discontinuous buffer electrophoretic system comprising:
an electrophoretic separation gel, said electrophoretic separation gel comprising a gel buffer system, said buffer system comprising:
a gel amine buffer selected from Bis-Tris, Bis-Tris propane, triethanolamine, and salts or combinations thereof at concentrations of about 200 mM to about 300 mM; and
a gel ampholyte selected from tricine, bicine, HEPPS, glycinamide, TAPS and salts or combinations thereof at concentrations of from about 50 mM to about 100 mM; and
an aqueous running buffer comprising a buffer ampholyte,
wherein the gel ampholyte is different from the buffer ampholyte.

25. The system of claim 1, wherein electrophoresis can be carried out at voltages of about 225 V and above.

26. The system of claim 25, where electrophoresis can be carried out at from about 225V to about 350 V.

* * * * *

UNITED STATES PATENT AND TRADEMARK OFFICE
CERTIFICATE OF CORRECTION

PATENT NO. : 11,105,769 B2
APPLICATION NO. : 16/551364
DATED : August 31, 2021
INVENTOR(S) : Timothy Updyke et al.

It is certified that error appears in the above-identified patent and that said Letters Patent is hereby corrected as shown below:

In the Claims

In Column 24, Claim 12, Line 31, delete "according to either of claim 1," and insert -- according to claim 1, --, therefor.

In Column 24, Claim 18, Line 55, delete "IVIES," and insert -- MES, --, therefor.

In Column 24, Claim 19, Line 61, delete "5 wt," and insert -- 5 wt. %, --, therefor.

In Column 25, Claim 26, Line 31, delete "225V" and insert -- 225 V --, therefor.

Signed and Sealed this
Third Day of May, 2022

Katherine Kelly Vidal
*Director of the United States Patent and Trademark Office*